US009132198B2

(12) United States Patent
Kelley et al.

(10) Patent No.: US 9,132,198 B2
(45) Date of Patent: *Sep. 15, 2015

(54) MITOCHONDRIAL PENETRATING PEPTIDES AS CARRIERS FOR ANTICANCER COMPOUNDS

(75) Inventors: Shana Kelley, Toronto (CA); Mark Pereira, Toronto (CA); Sonali Fonseca, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/700,970

(22) PCT Filed: May 27, 2011

(86) PCT No.: PCT/CA2011/000610
§ 371 (c)(1),
(2), (4) Date: Mar. 15, 2013

(87) PCT Pub. No.: WO2011/150494
PCT Pub. Date: Dec. 8, 2011

(65) Prior Publication Data
US 2013/0172266 A1 Jul. 4, 2013

(51) Int. Cl.
*C07K 7/06* (2006.01)
*C07K 5/10* (2006.01)
*A61K 47/48* (2006.01)
*A61P 35/00* (2006.01)
*A61K 38/00* (2006.01)

(52) U.S. Cl.
CPC ........... *A61K 47/48* (2013.01); *A61K 47/48246* (2013.01); *A61K 47/48315* (2013.01); *C07K 7/06* (2013.01); *A61K 38/00* (2013.01)

(58) Field of Classification Search
CPC ............ C07K 7/06; C07K 5/10; A61K 47/48; A61P 35/00
See application file for complete search history.

(56) References Cited

FOREIGN PATENT DOCUMENTS

| WO | WO 2007/108749 | 9/2007 |
| WO | WO 2009/036092 | 3/2009 |
| WO | WO 2009036092 A2 * | 3/2009 |

OTHER PUBLICATIONS

Ellerby, et al., "Anti-cancer activity of targeted pro-apoptotic peptides," Nature Med. 5:1032-1038 (1999).*
Horton et al., "Mitochondria-penetrating peptides," Chem. Biol. 15:375-382 (2008).*
Bielawski et al., Small-Molecule based Delivery Systems for Alkylating Antineoplastic Compounds, ChemMedChem 3:536-542 (2008).*
Hunter, A.M., et al., "The inhibitors of apoptosis (IAPs) as cancer targets" Apoptosis 12:1542-1568 (2007).*
Fonesca et al., "Recent advances in the use of cell-penetrating peptides for medical and biological applications," Adv. Drug. Deliv. Rev. 61:953-964 (2009).*
Shokolenko et al., "TAT-mediated protein transduction and targeted delivery of fusion proteins into mitochondria of breast cancer cells", DNA Repair 4:511-518 (2005)).*
Mae et al., "Cell-penetrating peptides as vectors for peptide, protein and oligonucleotide delivery", Curr. Opin. Pharmacol. 6:509-514 (2006).*
Property of Pep-I, p. 1, from STN, accessed Sep. 8, 2014.*
Property of Tat, p. 1, from STN, accessed Sep. 8, 2014.*
Allen and Coombs, "Covalent binding of polycyclic aromatic compounds to mitochondrial and nuclear DNA", *Nature*, 287(5779):244-245, 1980.
Anderson and O'Toole, "Innate and induced resistance mechanisms of bacterial biofilms", *Curr. Top Microbiol Immunol.*, 322:85-105, 2008.
Baba et al., "Construction of *Escherichia coli* K-12 in-frame, single-gene knockout mutants: the Keio collection", *Mol. Syst. Biol.*, 2:2006-2008, 2006.
Barbachyn and Ford, "Oxazolidinone structure-activity relationships leading to linezolid", *Angew Chem Int Ed Engl.*, 42:2010-2031, 2004.
Barnouin et al., "Multidrug resistance protein-mediated transport of chlorambucil and melphalan conjugated to glutathione", *Br. J. Cancer*, 77:201-209, 1998.
Begleiter et al., "Chlorambucil in Chronic Lymphocytic Leukemia : Mechanism of Action", *Leuk Lymphoma*, 23:187-201, 1996.
Carreon et al., "Cyanine dye conjugates as probes for live cell imaging", *Bioorganic & Medicinal Chemistry Letters*, 17:5182-5185, 2007.
Cullis et al., "Mechanism and reactivity of chlorambucil and chlorambucil—spermidine conjugate", *Chem. Soc. Perkin Trans.*, 2:1503-1511, 1995.
Davis et al., "Mitocondrial and Plasma Membrane Potentials Cause Unusual Accumulation and Retention of Rhodamine 123 by Human Breast Adenocarcinoma-derived MCF-7 Cells", *J. Biol. Chem*, 260:13844-13850, 1985.
Ellerby et al., "Anti-cancer activity of targeted pro-apoptotic peptides", *Nature Medicine*, 5(9):1032-1038,1999.
Espinosa-Mansilla et al., "Kinetic fluorimetric determination of the antineoplastic methotrexate (MTX) in human serum", *J. Pharm. Biomed. Anal*, 29:851-858, 2002.
Fan et al., "Cytokine response gene 6 induces p21 and regulates both cell growth and arrest", *Oncogene*, 18:6573-6582, 1999.
Fox and Stover, "Folate-mediated one-carbon metabolism", *Vitam Horm*, 79:1-44, 2008.
Frezza et al., "Organelle isolation : functional mitochondria from mouse liver, muscle and cultured filroblasts", *Nat. Protoc.*, 2:287-295, 2007.

(Continued)

*Primary Examiner* — Julie Ha
*Assistant Examiner* — Kristina M Hellman
(74) *Attorney, Agent, or Firm* — Norton Rose Fulbright US LLP

(57) ABSTRACT

There is described herein compounds comprising a mitochondrial penetrating peptide (MPP) conjugated to an anticancer compound, and their method of use.

20 Claims, 16 Drawing Sheets

(56) References Cited

OTHER PUBLICATIONS

Hamilton-Miller, "Antimicrobial activity of 21 anti-neoplastic agents", *Br J. Cancer*, 49:367-369, 1984.
Hanahan and Weinberg, "The Hallmarks of Cancer", *Cell*, 100:57-70, 2000.
Horton and Kelley, "Engineered Apoptosis-Inducing Peptides with Enhanced Mitochondrial Localization and Potency", *Med. Chem.*, 52:3293-3299, 2009.
Horton et al., "Mitochondria-penetrating peptides", *Chemistry and Biology*, 15(4):375-382, 2008.
Horton et al., "Characterization of a Chlorambucil-Resistant Human Ovarian Carcinoma Cell Line Overexpressing Glutathione S-Transferase m", *Biochem Pharmacol.*, 58 :693-702, 1999.
International Search Report issued in PCT Application No. PCT/CA2011/000609, mailed Sep. 2, 2011.
International Search Report issued in PCT Application No. PCT/CA2011/000610, mailed Sep. 12, 2011.
La Plante and Rybak, "Daptomycin—a novel antibiotic against Gram-positive pathogens", *Expert Opin Pharmacother*, 5:2321-2331, 2004.
Lakshmipathy and Campbell, "The Human DNA Ligase III Gene Encodes Nuclear and Mitochondrial Proteins", *Mol. Cell. Biol.*, 19(5):3869-3876, 1999.
Lowe and Lin, "Apoptosis in Cancer", *Carcinogenesis*, 21(3):485-495, 2000.
Lu et al., "GADD45gamma mediates the activation of the p38 and JNK MAP kinase pathways and cytokine production in effector TH1 cells", *Immunity*, 14(5):583-590, 2001.
Minn et al., "Expression of Bel-xL Can Confer a Multidrug Resistance Phenotype", *Blood*, 86 :1903-1910, 1995.
Modica-Napolitano and Aprille, "Delocalized lipophilic cations selectively target the mitochondria of carcinoma cells", *Adv. Drug Deliv. Rev.*, 49(1-2):63-70, 2001.
Modica-Napolitano and Aprille, "Basis for the Selective Cytotoxicity of Rhodamine 123", *Cancer Res.*, 47:4361-4365, 1987.
Modica-Napolitano et al., "Selective Damage to Carcinoma Mitochondria by Rhodacyanine MKT-077", *Cancer Res.*, 56 :544-550, 1996.
Muratovska et al., "Targeting large molecules to mitochondria", *Adv. Drug Deliv. Rev.*, 49:189-198, 2001.
Myrberg et al., "Design of a Tumor-Homing Cell-Penetrating Peptide", *Bioconjug. Chem.*, 19 :70-75, 2008.
Pepper et al., "Chlorambucil resistance in B-cell chronic lymphocytic leukaemia is mediated through failed Bax induction and selection of high Bcl-2-expressing subclones", *Br. J. Haematol*, 104 :581-588, 1999.
Pereira and Kelley, "Maximizing the therapeutic window of an antimicrobial drug by imparting mitochondria sequestration in human cells", *Journal of the American Chemical Society*, 133(10):3260-3263, 2011.
Petrini et al., "Reversing of chloramucil resistance by ethacrynic acid in a B-CLL patient", *Br J. Haematol.*, 85 :409-410, 1993.
Pignatello et al., "Lipophilic methotrexate conjugates with antitumor activity", *Eur J. Pharm Sci.*, 10:327-345, 2000.
Preston et al., "Mitochondrial contributions to cancer cell physiology: potential for drug development", *Adv. Drug Deliv. Rev.*, 49:45-61, 2001.

Reed, "Bcl-2 family proteins", *Oncogene*, 17 :3225-3236, 1998.
Santos et al., "Cell Sorting Experiments Link Persistent Mitochondrial DNA Damage with Loss of Mitochondrial Membrane Potential and Apoptotic Cell Death", *J. Biol. Chem.*, 278 :1728-1734, 2003.
Santos et al., "Quantitative PCR-based measurement of nuclear and mitochondrial DNA damage and repair in mammalian cells", *Methods Mol. Biol.*, 314 :183-199, 2006.
Schneider et al., "Virulence gene identification by differential fluorescence induction analysis of *Staphylococcus aureus* gene expression during infection-simulating culture", *Infect Immun.*, 70:1326-33, 2002.
Singh and Maniccia-Bozzo, "Evidence for lack of mitochondrial DNA repair following cisdichlorodiammineplatinum treatment", *Cancer Chemother Pharmacol.*, 26(2):97-100, 1990.
Smith and Fornance, "Mammalian DNA damage-inducible genes associated with growth arrest and apoptosis", *Mutat. Res.*, 340(2-3):109-124, 1996.
Sunters et al., "The cytotoxicity, DNA crosslinking ability and DNA sequence selectivity of the aniline mustards melphalan, chlorambucil and 4-[bis(2-chloroethyl)amino] benzoic acid", *Biochem. Pharmacol.*, 44(1):59-64, 1992.
Taubes, "Collateral damage. The rise of resistant C. difficile", *Science*, 321:360, 2008.
Taylor et al., "Apoptosis: controlled demolition at the cellular level", *Nat. Rev. Mol. Cell. Biol.*, 9 :231-241, 2008.
Trombe, "Entry of methotrexate into *Streptococcus pneumonia*: a study on a wild-type strain and a methotrexate resistant mutant", *J Gen Microbiol*, 131:1273-1278, 1985.
Uehara, "Natural product origins of Hsp90 inhibitors", *Current Cancer Drug Targets*, 3(5):325-330, 2003.
Weigel et al., "Genetic analysis of a high-level vancomycin-resistant isolate of *Staphylococcus aureus*", *Science*, 302:1569-1571, 2003.
Wipf et al., "Mitochondrial targeting of selective electron scavengers: synthesis and biological analysis of hemigramicidin-TEMP conjugates", *Journal of the American Chemical Society*, 127(36):12460-12461, 2005.
Wright et al., "Mechanisms of resistance to antibiotics", *Curr. Opin. Chem. Biol.*, 7 :563-569, 2003.
Yang et al., "Role of glutathione and glutathione S-transferase in chlorambucil resistance", *Mol. Pharmacol.*, 41 :625-630, 1992.
Yousif et al., "Mitochondria-penetrating peptides: sequence effects and model cargo transport", *Chembiochem : a European journal of chemical biology*, 10(12):2081-2088, 2009.
Chamberlain, et al., *ACS Chem.* 8:1380-95, 2013.
Del Gaizo, et al., *Mol Genet Metab.* 80(1-2):170-80, 2003.
Extended European Search Report issued in Application No. 11789003.8 mailed Oct. 8, 2013.
Fonseca, et al., *Chem & Biology*. 18:445-53, 2011.
Horton, et al., *Chem & Biol*. 15:375-82, 2008.
Lemeshko, et al., *Arch Biochem Biophys*. 493(2):213-220, 2010.
Modica-Napolitano, et al., *Expert Review in Mol Med*. (02):00445-3a, 2002.
Mourtada, et al., *PLOS One*. 8(4):e60253, 2013.
Fulda et al., *Nat Rev Drug Discov*. 9(6):447-464, 2010.
Tetko, et al., *J Computer-Aided Mol Design*. 19:453-3, 2005.
Wisnovsky, et al., *Chem & Biol*. 20:1323-8, 2013.
Yousif, et al., *ChemBioChem*. 10:2081-8, 2009.

\* cited by examiner

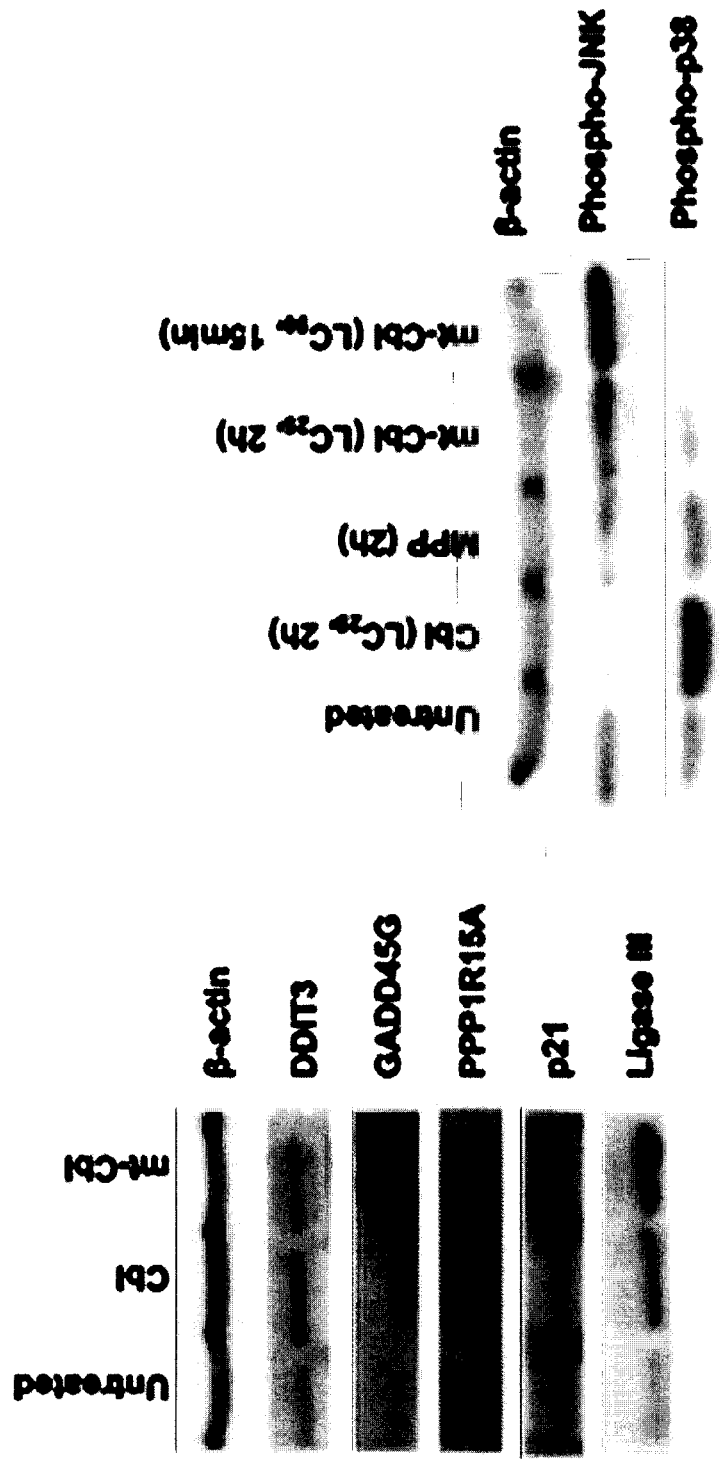

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: Cyclohexylalanine
<220> FEATURE:
<221> NAME/KEY: MISC_FEATURE
<222> LOCATION: (3)..(3)
<223> OTHER INFORMATION: Cyclohexylalanine
<220> FEATURE:
<221> NAME/KEY: MISC_FEATURE
<222> LOCATION: (5)..(5)
<223> OTHER INFORMATION: Cyclohexylalanine
<220> FEATURE:
<221> NAME/KEY: MISC_FEATURE
<222> LOCATION: (7)..(7)
<223> OTHER INFORMATION: Cyclohexylalanine

<400> SEQUENCE: 1

Ala Arg Ala Lys Ala Arg Ala Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Cyclohexylalanine
<220> FEATURE:
<221> NAME/KEY: MISC_FEATURE
<222> LOCATION: (3)..(3)
<223> OTHER INFORMATION: Cyclohexylalanine
<220> FEATURE:
<221> NAME/KEY: MISC_FEATURE
<222> LOCATION: (7)..(7)
<223> OTHER INFORMATION: Cyclohexylalanine

<400> SEQUENCE: 2

Ala Arg Ala Lys Phe Arg Ala Lys
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Cyclohexylalanine
<220> FEATURE:
<221> NAME/KEY: MISC_FEATURE
<222> LOCATION: (3)..(3)
<223> OTHER INFORMATION: Cyclohexylalanine

<400> SEQUENCE: 3

Ala Arg Ala Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Cyclohexylalanine
<220> FEATURE:
```

```
<221> NAME/KEY: MISC_FEATURE
<222> LOCATION: (3)..(3)
<223> OTHER INFORMATION: Diphenyl

<400> SEQUENCE: 4

Ala Arg Xaa Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Cyclohexylalanine
<220> FEATURE:
<221> NAME/KEY: MISC_FEATURE
<222> LOCATION: (3)..(3)
<223> OTHER INFORMATION: Napthyl

<400> SEQUENCE: 5

Ala Arg Xaa Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Cyclohexylalanine
<220> FEATURE:
<221> NAME/KEY: MISC_FEATURE
<222> LOCATION: (3)..(3)
<223> OTHER INFORMATION: Hexyl

<400> SEQUENCE: 6

Ala Arg Xaa Lys
1

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Cyclohexylalanine
<220> FEATURE:
<221> NAME/KEY: MISC_FEATURE
<222> LOCATION: (3)..(3)
<223> OTHER INFORMATION: Cyclohexylalanine
<220> FEATURE:
<221> NAME/KEY: MISC_FEATURE
<222> LOCATION: (5)..(5)
<223> OTHER INFORMATION: Cyclohexylalanine

<400> SEQUENCE: 7

Ala Arg Ala Arg Ala Arg
1               5

<210> SEQ ID NO 8
<211> LENGTH: 23
```

```
<212> TYPE: DNA
<213> ORGANISM: Artificial Sequence
<220> FEATURE:
<223> OTHER INFORMATION: Synthetic Primer

<400> SEQUENCE: 8
gaaatgaagc gagtcacaaa agc                                              23

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
gtacccttca catccttcag c                                                21

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
cctcatcccg tgttctcctt t                                                21

<210> SEQ ID NO 11
<211> LENGTH: 14
<212> TYPE: DNA
<213> ORGANISM: Artificial Sequence
<220> FEATURE:
<223> OTHER INFORMATION: Synthetic Primer

<400> SEQUENCE: 11
cccagcggac aagt                                                        14

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
caacggattt ggtcgtattg g                                                21

<210> SEQ ID NO 13
<211> LENGTH: 28
<212> TYPE: DNA
<213> ORGANISM: Artificial Sequence
<220> FEATURE:
<223> OTHER INFORMATION: Synthetic Primer

<400> SEQUENCE: 13
gcaacaatat ccactttacc agagttaa                                         28
```

MITOCHONDRIAL PENETRATING PEPTIDES AS CARRIERS FOR ANTICANCER COMPOUNDS

CROSS REFERENCE TO RELATED APPLICATIONS

This application is a national phase application under 35 U.S.C. §371 of International Application No. PCT/CA2011/000610 filed May 27, 2011, which claims priority to U.S. Provisional Patent Application Ser. No. 61/349,881 filed May 30, 2010, both of which are incorporated herein by reference in their entirety.

FIELD OF THE INVENTION

This invention relates to cell-permeable peptides that localize to the mitochondria and their use as carriers for anticancer compounds.

BACKGROUND OF THE INVENTION

The energy-producing capacity of mitochondria is contingent on the preservation of a barrier limiting the permeation of ions or other small molecules. The highly hydrophobic, densely packed structure of the inner mitochondrial membrane is impenetrable to most molecular species—a property critical for the proton pumping that directs oxidative phosphorylation[1]. The impermeability of the inner membrane has impeded the delivery of drug molecules that could target the other important biological role of mitochondria—apoptotic triggering[2]. Given that apoptotic resistance is observed in many types of cancer cells[3], being able to intervene by targeting apoptotic factors to mitochondria could enable the development of new anticancer strategies.

SUMMARY OF THE INVENTION

According to one aspect, there is provided a compound comprising a mitochondrial penetrating peptide (MPP) conjugated to an anticancer compound.

According to a further aspect, there is provided the compound described herein for treating cancer.

According to a further aspect, there is provided a pharmaceutical composition comprising the compound described herein and a pharmaceutically acceptable carrier.

According to a further aspect, there is provided a library of compounds comprising a plurality of compounds described herein.

According to a further aspect, there is provided a method of treating cancer comprising administering to the subject a therapeutically effect amount of the composition described herein.

According to a further aspect, there is provided a use of the compound described herein in the preparation of a medicament for the treatment of cancer.

According to a further aspect, there is provided a use of the composition described herein for the treatment of cancer.

According to a further aspect, there is provided a method of inducing apoptosis in a cancer cell comprising administering a therapeutically effect amount of the composition described herein.

BRIEF DESCRIPTION OF THE DRAWINGS

Embodiments of the invention may best be understood by referring to the following description and accompanying drawings. In the description and drawings, like numerals refer to like structures or processes. In the drawings.

DETAILED DESCRIPTION

Figure 1A:
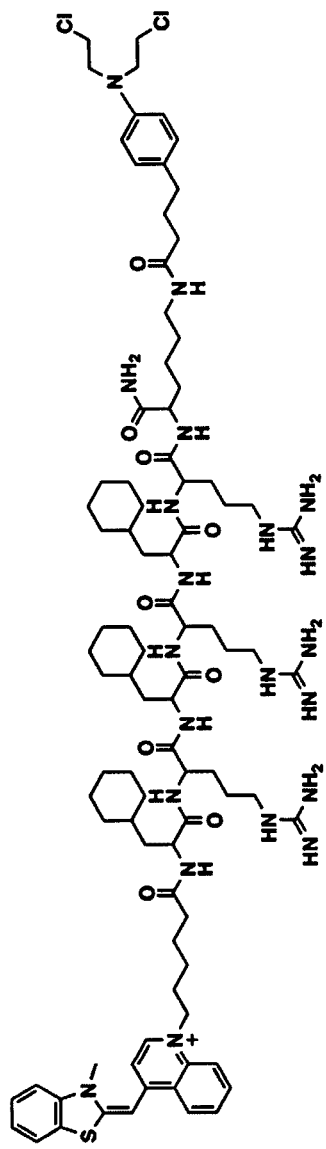
FIG. 1 shows mitochondrial localization and toxicity of mt-Cbl. (A) The structure of fluorescently labeled mt-Cbl conjugate used in studies of mitochondrial drug localization. In all other assays, an acetyl group replaced the thiazole orange (to) fluorophore on the peptide N-terminus. (B) Localization of MPP in mitochondrial matrix as observed by immunogold staining and TEM imaging of isolated mitochondria. Gold nanoparticles corresponding to the locations of biotinylated peptides within isolated mouse mitochondria are observed (note that the electron dense, darker regions represent the mitochondrial matrix under the conditions used for staining). (C) Quantitation of the results for 100s of mitochondria provide quantitative evidence for predominant matrix localization. (D) Intracellular localization of to-mt-Cbl in live HeLa cells compared with Mitotracker 633. (E) Toxicity of mt-Cbl towards HeLa cells after 24 hours of incubation. (F) Increased levels of superoxide observed with mitochondrial targeting of Cbl in HeLa cells. MitoSOX staining and assessment by flow cytometry was consistent with increased superoxide. (G) Mitochondrial delivery of Cbl depolarizes the mitochondrial membrane in HeLa cells. Mitochondrial membrane potential was analyzed by flow cytometry of JC-1 staining. Mean values plotted, n=3, error bars are s.e.m. Two-tailed t-test used to determine P values.

In the following description, numerous specific details are set forth to provide a thorough understanding of the invention. However, it is understood that the invention may be practiced without these specific details.

The difficulty of accessing the mitochondrial matrix has limited the targeting of anticancer therapeutics to this organelle. Here, we report the successful delivery of the alkylating agent chlorambucil to mitochondria using a synthetic peptide carrier. Mitochondrial targeting of this agent dramatically potentiates its activity, and promotes apoptotic cell death in a variety of cancer cell lines and patient samples with retention of activity even in cells with drug resistance or disabled apoptotic triggering.

According to one aspect, there is provided a compound comprising a mitochondrial penetrating peptide (MPP) conjugated to an anticancer compound.

"Anticancer compounds" includes any substance administered for the treatment of cancer. Typically, the majority of chemotherapeutic drugs can be divided in to alkylating agents, antimetabolites, anthracyclines, plant alkaloids, topoisomerase inhibitors, and other antitumour agents. Preferable anticancer agents according to the disclosed aspects and used in connection with MPPs include the following.

| Mechanism of Action | Class of Drugs | Examples of potential drugs |
|---|---|---|
| DNA intercalators | Isoquinoline alkaloids | Berberine |
| | Acridines | Proflavine |
| | Anthracyclines | Daunorubicin |
| | | Doxorubicin |
| | | Thalidomide |
| | Furocoumarins | Psoralen |
| | Other | Ethidium bromide |
| Alkylating agents | Nitrogen mustards | Melphalan |
| | | Bendamustine |
| | Nitrosoureas | carmustine |
| | Sulphur mustards | bis(2-chloroethyl sulfide) |
| | | sulfur sesquimustard |
| | Platinum compounds | Cisplatin |
| | | Satraplatin |
| | Aziridine-containing | Mitomycin |
| | Others | Dacarbazine |
| | | Mitozolomide |
| | | Temozolomide |
| Transcription inhibitors | Polypeptide antibiotics | Actinomycin D |
| DNA Enzyme Inhibitors | Topoisomerase inhibitors | Etoposide |
| | | Mitoxantrone |
| | | Amsacrine |
| | | Teniposide |
| | | Irinotecan |
| DNA synthesis inhibitor | DNA analogs | Fludarabine |
| | | Mercaptopurine |
| | | Thioguanine |
| | | Pentostatin |
| | | Cladribine |
| | | Floxuridine |
| Enzyme inhibitors | Glutathione S-transferase inhibitor | Etacrynic acid |
| | ATP synthase inhibitor | Oligomycin |

In some embodiments, the anticancer agent is conjugated to the C-terminus of the MPP. In other embodiments, the anticancer agent is conjugated to the N-terminus of the MPP.

In one embodiment, the compound is $F_x r3$-Cbl.

The present MPPs preferably possess both positive charge and lipophilic character, properties determined herein to be important for passage across both the plasma and mitochondrial membranes. Thus, MPPs contain cationic and hydrophobic residues to provide a positively charged lipophilic character that facilitates passage through both the plasma and mitochondrial membranes. Cationic amino acids such as lysine (K), arginine (R), aminophenylalanine, and ornithine may be incorporated within the MPPs to provide positive charge, while hydrophobic residues such as phenylalanine (F), cyclohexylalanine (Fx) aminooctaarginine (Hex), diphenylalanine ($F_2$) and (1-naphthyl)-L-alanine (Nap), may be incorporated within the MPPs to impart lipophilicity. Although the arrangement of charged and hydrophobic residues within an MPP is not particularly restricted provided the MPP possesses appropriate charge and lipophilicity to pass through the plasma and mitochondrial membranes, the MPPs may comprise alternating charged and hydrophobic residues to increase the level of lipophilicity within the MPP.

MPPs according to the invention may be made using well-established techniques of peptide synthesis, including automated or manual techniques, as one of skill in the art will appreciate.

The length of the present MPPs is not particularly restricted but will generally be of a length suitable for transport across plasma and mitochondrial membranes, either alone or conjugated to another entity such as a biological agent as will be described. Generally, the MPPs will be comprised of 4-20 residues.

The MPPs may include one or more residues modified to impart on the MPP desirable properties, for example, increased intracellular stability. In this regard, for example, the MPPs may include d-stereoisomers, and terminal modifications such as amide termini.

In some embodiments, the MPP can traverse the inner membrane of the mitochondria, preferably in a potential dependent manner.

In some embodiments, the MPP comprises a charge of +3 and a log P value of at least about −1.7.

In other embodiments, the MPP comprises a charge of +5 and a log P value of at least about −2.5.

Preferably, the MPP is any one of SEQ ID NOs. 1-7.

According to a further aspect, there is provided the compound described herein for treating cancer.

According to a further aspect, there is provided a pharmaceutical composition comprising the compound described herein and a pharmaceutically acceptable carrier.

According to a further aspect, there is provided a library of compounds comprising a plurality of compounds described herein.

According to a further aspect, there is provided a method of treating cancer comprising administering to the subject a therapeutically effect amount of the composition described herein.

According to a further aspect, there is provided a use of the compound described herein in the preparation of a medicament for the treatment of cancer.

According to a further aspect, there is provided a use of the composition described herein for the treatment of cancer.

According to a further aspect, there is provided a method of inducing apoptosis in a cancer cell comprising administering a therapeutically effect amount of the composition described herein.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The following examples are illustrative of various aspects of the invention, and do not limit the broad aspects of the invention as disclosed herein.

EXAMPLES

Methods

Cell Culturing Conditions.

HeLa cells were cultured in MEM alpha (Invitrogen, Carlsbad) supplemented with 10% (v/v) FBS at 37° C. with 5% $CO_2$. U937 cells were cultured in RPMI 1640+10% FBS and Iscove's Modified Dulbecco's Media+10% FBS was used for OCI-AML2, HL60, K562, OCI-M2, LY17 and Daudi. A2780 Wildtype and Cbl-Resistant Lines were cultured in RPMI 1640+10% FBS at 37° C. with 5% $CO_2$ and the Cbl-resistant line was treated with 100 μM Cbl once a week for 1 hour to maintain resistance.

Peptide Synthesis & Characterization.

Solid-phase synthesis was performed on Rink amide MBHA resin (0.7 mmol/g, 100-200 mesh) (NovaBiochem) using a Prelude Protein Technologies peptide synthesizer as described previously.[25,26] Peptides were synthesized on a 25 μmol or 50 μmol scale. Thiazole orange (to) was synthesized as described previously[27] and coupled to peptides using HBTU (4 eq, Protein Technologies, Tucson), HBTU=O-(benzotriazol-1-yl)-N,N,N',N'-tetramethyl-uronium hexafluorophosphate), and DIPEA (8 eq, Sigma-Aldrich, St. Louis), DIPEA=N,N-diisopropylethylamine) in N,N-dimethyl formamide (DMF) overnight. Chlorambucil (Sigma-Aldrich, St. Louis) was coupled to peptides using HBTU (4 eq) and DIPEA (4 eq) in DMF. The N-terminus of unlabeled peptides was capped using acetic anhydride, pyridine and DCM (1:5:10, Sigma). Peptides were deprotected and cleaved from the resin using TFA:triisopropylsilane:$H_2O$ (95:2.5:2.5) and precipitated in cold ether. All peptides were purified to >95% purity by RP-HPLC on a C18 column with a $H_2O$/MeCN gradient in 0.1% TFA and identity confirmed by electrospray ionization mass spectroscopy. Peptides containing chlorambucil were immediately flash frozen in liquid nitrogen post purification and lyophilied to dryness. Thiazole orange labeled peptides were quantified at 500 nm using an extinction coefficient of 63,000 $M^{-1}cm^{-1}$.[2] Chlorambucil conjugated peptides were quantified at 258 nm using the chlormabucil extinction coefficient of 15200 $M^{-1}cm^{-1}$.[28] Unlabeled peptides were quantified using a BCA assay (Pierce, Rockford).

TABLE 1

List of Peptide Conjugates

| Compound | Peptide Sequence |
| --- | --- |
| to-mt-Cbl | TO-$F_xrF_xrF_x$rk-Cbl |
| mt-Cbl or MPP-Cbl | Ac-$F_xrF_xrF_x$rk-Cbl |
| MPP | Ac-$F_xrF_xrF_x$r |
| to-MPP | TO-$F_xrF_xrF_x$r |
| Biotin-MPP | Biotin-$F_xrF_xrF_x$r |
| Biotin-mt-Cbl | Cbl-$F_xrF_xrF_x$rk-Biotin |

Confocal Microscopy—Live Cells.

Cells were seeded in 8 well μ-slides (iBidi, Germany) at a density of 25,000 cells per well one day prior to experiments. Peptide incubations (5 μM) were performed for the indicated times in OPTI-MEM (Invitrogen, Carlsbad) supplemented with 2% (v/v) FBS. Where stated, Mitotracker 633 (Invitrogen, Carlsbad) was added for the last 20 min of the incubation. Cells were then washed twice and imaged using an inverted Zeiss LSM 510 confocal microscope.

Confocal Microscopy—Fixed Cells.

HeLa cells were plated as above and treated with 5 μM peptide in MEM alpha without phenol red for 5 min at 37° C. with 5% $CO_2$. Peptide solutions were then removed and replaced with fresh media for 25 min at 37° C. with 5% $CO_2$. Cells were washed twice with PBS and incubated with acetone for 10 min at −20° C. Cells were again washed twice with PBS, incubated with 0.1% Triton X-100 for 5 min at 4° C., washed with PBS and imaged as above. Where stated, cells were incubated with 10 units DNase in 1×DNase buffer for 2 hours at 37° C. prior to imaging.

TEM Imaging.

Mitochondria were isolated from fresh mouse liver as previously described[1]. Functionality was confirmed using respirometry. The isolated organelles were used only when the levels of oxygen consumption in state III respiration (presence of ADP) were >4 fold greater than in state II respiration, indicating well-coupled mitochondria. Mitochondrial protein concentration was determined by BCA assay (Sigma). Mitochondria were diluted to 0.5 mg/mL in PBS and incubated for 20 minutes at 25° C. with biotin-$F_xrF_xrF_x$r. Cold PBS was added and mitochondria were pelleted by centrifugation. The pellet was fixed in 1% glutaraldehyde in PBS for 90 min at room temperature, washed with PBS, then fixed with 1% osmium tetroxide for 2 hr at 4° C. The pellets were dehydrated using graded ethanol, followed by stepwise infiltration with propylene oxide and Epon-Araldite resin. The pellets were cured in resin for 48 hr at 60° C. The blocks were sectioned to 60 nm and the sections adhered to nickel grids for 30 min at 60° C. The grids were floated on saturated aqueous sodium metaperiodate for an hour at room temperature, washed, then blocked with 1% BSA, and labeled with Anti-biotin (Jackson Immunolabs) followed by Protein A-gold (Aurion, 10 nm). The grids were rinsed with water and stained with 2% uranyl acetate for 5 minutes. To quantitate gold labeling, 200 gold particles (for more densely labeled samples) or 400 mitochondria (for less densely labeled samples) were counted for each counting event. A minimum of three counting events was performed per sample. Counting was performed over different sections.

Analysis of Toxicity.

HeLa cells were seeded in 96-well flat bottom tissue culture plates (Starstedt, Germany) at a density of 12,000 cells per well. Leukemic cell lines (K562, OCI-M2, U937, HL60, AML2, LY17, Daudi) were seeded in 96-well flat bottom plates (CellStar, locato) at a density of 50,000 cells per well. A2780 wildtype and A2780 Cbl-resistant cells were plated in 96-well flat bottom tissue culture plates (Starstedt, Germany) at 25,000 cells per well. The culture media was removed and cells were washed. Peptide incubations were conducted in cell appropriate media, HeLa cell incubations were conducted in OPTI-MEM media. Cellular viablity was analyzed after an overnight incubation at 37° C. with 5% $CO_2$ using the CCK-8 viability dye (Dojindo, Rockville) at an absorbance of 450 nm. Statistical analysis was done using Graphpad Prism Software (Graphpad, La Jolla).

Analysis of Mitochondrial Superoxide Levels.

HeLa cells were plated at 100,000 per well of a 24-well plate 24 hours prior to experiment and treated with Cbl or MPP-Cbl in OPTI-MEM (Invitrogen, Carlsbad) for 1 hour. Media was removed and cells were incubated with MitoSox (Invitrogen, Carlsbad) according to manufacturer's instructions. Cells were washed with PBS, trypsinized and analyzed via flow cytometry with FACSCanto (BD, Franklin Lakes).

Annexin V Apoptosis Assay.

Leukemic cell lines (K562, OCI-M2, U937, HL60) were seeded at 200,000 cells per well of a 24-well plate (Greiner Bio-one, Germany). A2780 WT and Cbl-resistant cells were plated in 24-well plate at a density of 75,000 cells per well (BD, Franklin Lakes). Healthy donor mononuclear cells were obtained by Ficoll separation from peripheral blood. CLL patient samples, PBSCs, and healthy donor mononuclear cells were plated at 200,000 per well (Greiner Bio-one, Germany). Cells were incubated in triplicate with peptides at concentrations indicated in cell appropriate media. Following overnight incubation at 37° C. with 5% $CO_2$, cells were stained with Annexin V-FITC (BD Pharmingen, Franklin Lakes) and Styox Red (Invitrogen, Carlsbad) according to manufacturer's instructions. Flow cytometry was performed using a FACSCanto (BD, Franklin Lakes). Apoptoic induction by staurosporine was accomplished by addition of 3 μM staurosporine (Sigma-Aldrich, St. Louis) with an overnight incubation.

Western Blots.

Leukemia cells were cultured as above and were washed twice with PBS prior to lysis (10 mM Tris, 200 mM NaCl, 1 mM EDTA (pH 7.4), 1 mM PMSF, 0.5% NP-40, 1% Triton X-100, 1× Protease Inhibitor Cocktail (Bioshop, Burlington, ON)) at 4° C., 30 min. Cells were then centrifuged at 1,200 rcf, 4° C., 5 min and protein levels were quantified using bicinchoninic acid (BCA) assay (Pierce, Rockford). 15 μg of total protein was diluted in 8× sample buffer and heated to 42° C. for 5 min prior to loading on 15% gel. Gels were run at 100 V for 1 h, and then proteins were transferred onto nitrocellulose membrane at 100 V for 40 min. Membranes were blocked with 5% skim milk for 1 hour and then probed with primary antibody according to manufacturer's instructions (1:500 $Bcl_{XL}$ antibody [Abcam, Cambridge, Mass.], 1:2000 β-actin antibody [Abcam], 1:1000 phospho INK [Abcam], 1:1000 phospho p38 [Abcam], 1:1000 GADD45G [Santa Cruz Biotechnology, Santa Cruz, Calif.], 1:1000 PPP1R15A [Santa Cruz Biotechnology], 1:1000 DNA Ligase III [Santa Cruz Biotechnology], 1:1000 p21 [Santa Cruz Biotechnology], and 1:1000 DDIT3 [Cell Signaling Technology, Beverly, Mass.]). Membranes were then washed and incubated with 1:5000 donkey anti-mouse or goat anti-rabbit IgG-HRP secondary antibody for 1 hr prior to ECL chemiluminescence detection (GE Amersham).

Hemolysis Assay.

Red blood cells obtained during Ficoll separation of healthy donor peripheral blood was used for this assay. Cells were washed with PBS until the supernatant was clear. Peptide solutions were made in Iscove's media and a 1:2 dilution was made across a 96-well plate. To each well, 2 μl, of red blood cells were added, mixed and then incubated for 1 hour at 37° C. with 5% $CO_2$. For 100% lysis, 0.1% Triton X-100 was added to three wells and for 0% lysis, cells from three wells without peptide were used. Plates were spun at 1000×g for 10 min and 50 μL of supernatant was then transferred to a new plate, mixed with 50 μL of PBS and read at 415 nm.

Peptide Uptake.

CLL patient samples, PBSCs and healthy donor B cells were seeded at 200,000 cells per well in triplicate in a 24-well plate in Iscove's media. Cells were then incubated with 5 μM thiazole orange-labeled peptide for 15 min, washed with PBS and analyzed on FACSCanto (BD, Franklin Lakes) to determine relative intracellular peptide concentrations.

Mitochondrial Membrane Potential.

HeLa cells were seeded at 50,000 cells per well 24 hours prior to experiment. CLL patient samples, PBSCs and healthy donor B cells were seeded at 200,000 cells per well in triplicate in a 24-well plate in Iscove's media. Cells were then incubated with 2 μM of 5,5',6,6'-tetrachloro-1,1',3,3'-tetraethylbenzimidazolylcarbocyanine iodide (JC-1, Invitrogen, Carlsbad) for 20 minutes at 37° C. Each sample was then washed twice with 1 mL PBS and resuspended in 300 μL PBS prior to being read on a BD FACS Canto. Samples were excited at 488 nm and emission was collected at 526 nm (green) and 595 nm (red). To obtain the mitochondrial membrane potential (red/green), emission from the red channel was divided by emission from the green channel. For membrane depolarization studies, HeLa cells were treated with Cbl or MPP-Cbl for 1 hour in OPTI-MEM (Invitrogen, Carlsbad) prior to incubation with JC-1. Cells were washed with PBS, trypsinized and analyzed as above.

Colorimetric Alkylation Assay.

Alkylation was tested using 4-(4-Nitrobenzyl)pyridine (4-NBP) (Thomas, et al., 1992). Briefly, compound (200-450 μM) was incubated with 4-NBP (0.7% w/vol) in a buffer containing 85 mM triethanolamine (pH 7.2) and 43% acetone. Reactions were incubated at 37° C. for 30-120 min. Reactions were terminated by freezing in a dry ice/ethanol bath. To develop samples, 100 ml ethyl acetate and 25 μl 5N NaOH were added followed by vortexing. Absorbance of organic ethyl acetate was read at 540 nm.

Crosslinking of Isolated DNA.

Crosslinking of isolated pBR322DNA was determined from a modification of a published method.[30] Briefly, pBR322DNA was incubated with compounds at concentrations and times indicated in 25 mM triethanolamine (pH 7.2) and 1 mM EDTA. Reactions were terminated by the addition of 50 mM EDTA and 150 μg/ml excess short oligonucleotide DNA. Samples were denatured at 95° C. in denaturation buffer (30% DMSO, 1 mM EDTA, bromophenol blue, xylene cyanol, and 0.4% SDS) for 3 min and flash frozen in a dry ice/ethanol bath. Electrophoresis was carried out in 0.8% agarose in TAE buffer and stained post-run with ethidium bromide.

Quantitative Real-Time PCR.

Six hundred thousand HL60 cells were incubated in Iscove's media (Invitrogen) with Cbl, mt-Cbl, or MPP at the LC25 dose (17, 3, and 3 μM, respectively) for either 2 or 24 hr as indicated. For Lig3, cells were incubated at an LC50 dose (34, 6, and 6 μM, respectively) for 1 hr. RNA was then isolated using the RNeasy Mini-Kit (QIAGEN, Hilden, Germany) according to the manufacturer's instructions. RNA was quantified on a NanoDrop, and 1 μg was converted to cDNA using the RT2 First Strand Kit (SA Biosciences, Frederick, Md.). qPCR was then performed using the Human DNA Damage Signaling Pathway PCR Array (PAHS-029; SA Biosciences) or with selected primers purchased from SA Biosciences according to manufacturer's instructions. Data analysis was performed using the web-based software provided by SA Biosciences. Lig3, p21, and GAPDH primers were designed independently: LIG3, forward GAAATGAAGCGAGTCA-CAAAAGC (SEQ ID NO. 8) and reverse GTACCCTTCA-CATCCTT CAGC (SEQ ID NO. 9); p21, forward CCT-CATCCCGTGTTCTCCTTT (SEQ ID NO. 10) and reverse GTACCA CCCAGCGGACAAGT (SEQ ID NO. 11); and GAPDH, forward CAACGGATTTGGTCGTATTGG (SEQ ID NO. 12) and reverse GCAACAATATCCACTTTACCA-GAGTTAA (SEQ ID NO. 13). All other steps were performed in an analogous manner to the method described above. Genes showing ≥4-fold change in expression levels compared to control cells were considered hits, as recommended by the SA Biosciences' manufacturer. All hits were confirmed with three biological replicates using primers purchased from SA Biosciences.

Determination of DNA Lesion Frequency by Quantitative PCR.

A total of $5 \times 10^6$ HL60 cells were treated with Cbl (150 μM) or mt-Cbl (3 μM) for 2 hr. DNA was isolated from frozen cell pellets with the QIAGEN Genomic Tip and Genomic DNA Buffer Set Kit (QIAGEN) and quantified using the PicoGreen dye (Invitrogen). Quantitative amplification of the 8.9 kb mitochondrial segment and the 17.7 kb β-globin target sequence was performed using the GeneAmp XL PCR kit (Perkin-Elmer) as described previously[31]. Lesion frequency at a given dose, D, was calculated as D=–ln AD/AC, where AD is the amplification at the dose, and AC is the level of amplification in nondamaged controls.

Collection of Patient Samples.

Peripheral blood cells from normal individuals and patients with CLL were collected following written informed consent according to a research ethics board (REB) approved protocol. Mononuclear cells were isolated by Ficoll-Hypaque centrifugation. The cells were either used fresh or stored in a viable state at –150° C. in 10% DMSO, 40% FBS, and alpha medium. PBSCs were excess filgrastim-mobilized cells obtained from stem cell transplant donors obtained according to an REB approved protocol.

Results and Discussion

In an effort to provide carriers for mitochondrial delivery of bioactive cargo, Horton, K. L., Stewart, K. M., Fonseca, S. B., Guo, Q. & Kelley, S. O. *Chem Biol* 15, 375-82 (2008) described mitochondria-penetrating peptides (MPPs) that can efficiently traverse both the plasma membrane and mitochondria membranes with a variety of attached cargos[4,5].

Horton, K. L., Stewart, K. M., Fonseca, S. B., Guo, Q. & Kelley, S. O. Mitochondria-penetrating peptides. *Chem Biol* 15, 375-82 (2008), incorporated herein in its entirety by reference, includes SEQ ID NOs. 1-6 below.

TABLE 2

| Compound | SEQ ID NO. |
|---|---|
| $F_x$-r-$F_x$-K-$F_x$-r-$F_x$-K | 1 |
| $F_x$-r-$F_x$-K-F-r-$F_x$-K | 2 |
| $F_x$-r-$F_x$-K | 3 |
| $F_x$-r-$F_2$-K | 4 |
| $F_x$-r-Nap-K | 5 |
| $F_x$-r-Hex-K | 6 |
| $F_x$-r-$F_x$r-$F_x$-r | 7 |

$F_x$ = cyclohexylalanine
$F_2$ = diphenyl
Nap = napthyl
Hex = Hexyl

Here, we investigate the impact of mitochondrial delivery of a cargo with clinically-relevant anticancer activity, the nitrogen mustard chlorambucil (Cbl). Cbl is a potent alkylating agent that is used to treat leukemia and its activity is linked to alkylation of the nuclear genome[6]. Here, we report the targeting of this agent to the mitochondria and document the unique ability of this organelle-specific drug to evade two commonly observed resistance mechanisms that deactivate cancer therapeutics.

Cbl was selected as a preferable drug for mitochondrial delivery because it exhibits rapid reaction kinetics and does not require cellular activation. In addition, the carboxylic acid moiety provides an ideal functional group for facile attachment to an MPP. To generate a mitochondria-specific version of Cbl, the drug was coupled to a MPP with the sequence $F_xrF_xrF_xr$ (Fx=cyclohexylalanine, r=d-arginine) (FIG. 1A, Table 1). This peptide accesses the mitochondrial matrix (FIG. 1B) and therefore is a suitable vector for delivery of Cbl for mitochondrial DNA alkylation. This peptide is comprised entirely of artificial amino acids, which make it resistant to intracellular degradation. The peptide sequence was designed based on previous work indicating that the inclusion of cyclohexylalanine units within a sequence introduces sufficient hydrophobicity to allow penetration of the mitochondrial membranes, whereas cationic units drive uptake across the energized barrier enclosing mt[4]. The peptide was generated by conventional solid-phase synthesis, and the drug was then attached by coupling to a C-terminal lysine residue. Retention of the alkylation activity and DNA crosslinking activity of Cbl in the mitochondrially targeted conjugate were confirmed in vitro (FIGS. 8B and 8C). It was also confirmed that placing the drug at the N-terminus resulted in comparable effects with little change in activity of the MPP-drug conjugate (data not shown).

Figure 1B:
Figure 1C:
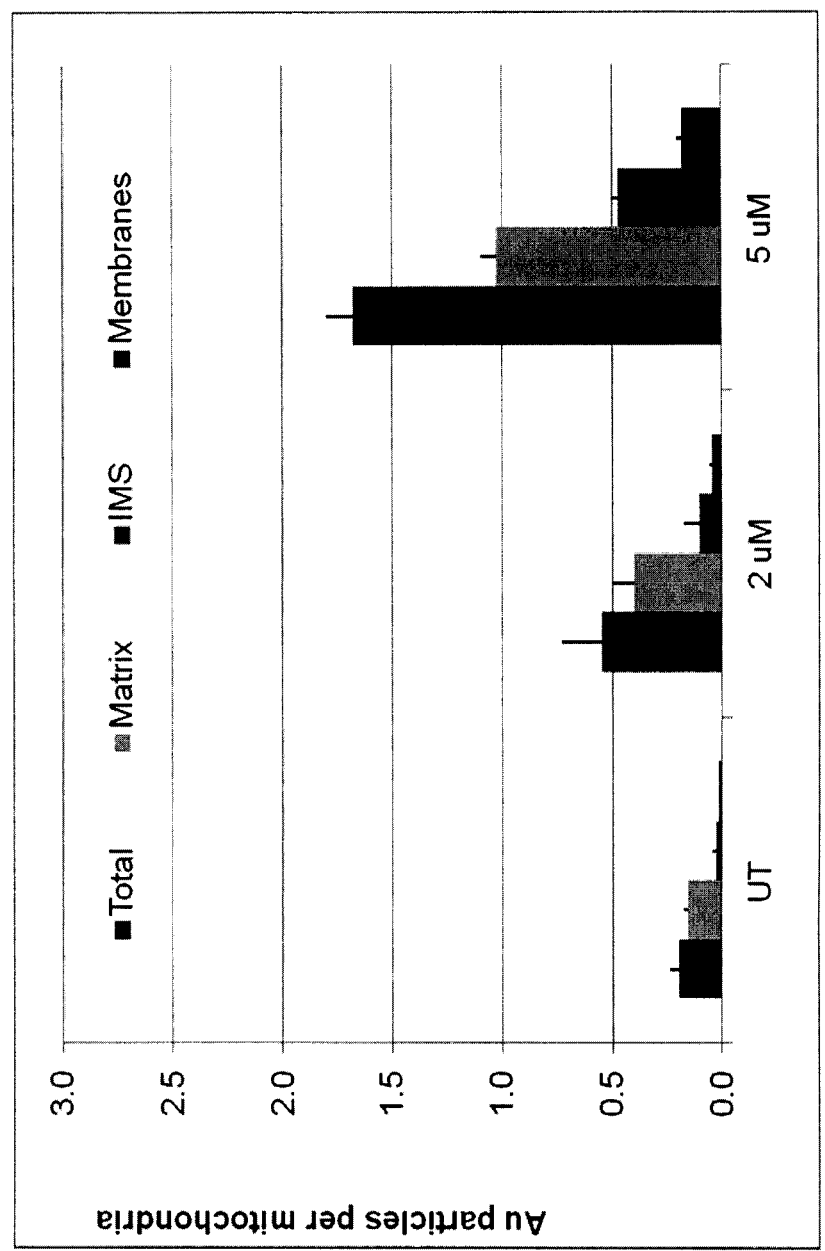
Figure 1D:
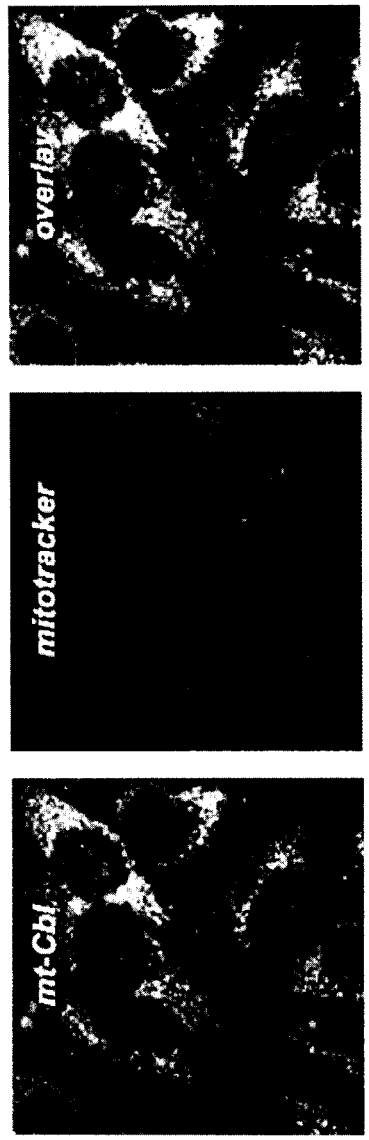

To test whether this MPP could efficiently deliver Cbl to the mitochondria, the fluorophore thiazole orange (to)[7] was coupled to the N-terminus to track intracellular localization (FIG. 1A). Penetration of the peptide into the mitochondrial matrix was confirmed with a biotinylated MPP that could be visualized by immunogold TEM (FIG. 1B). Quantitation of the results for 100s of mitochondria provided quantitative evidence for predominantly matrix localization (FIG. 1C). The intracellular localization in live HeLa cells strongly correlated with that of the mitochondria-specific dye Mitotracker, suggesting that Cbl successfully accumulated within the mitochondria (FIG. 1D).

Figure 8A:
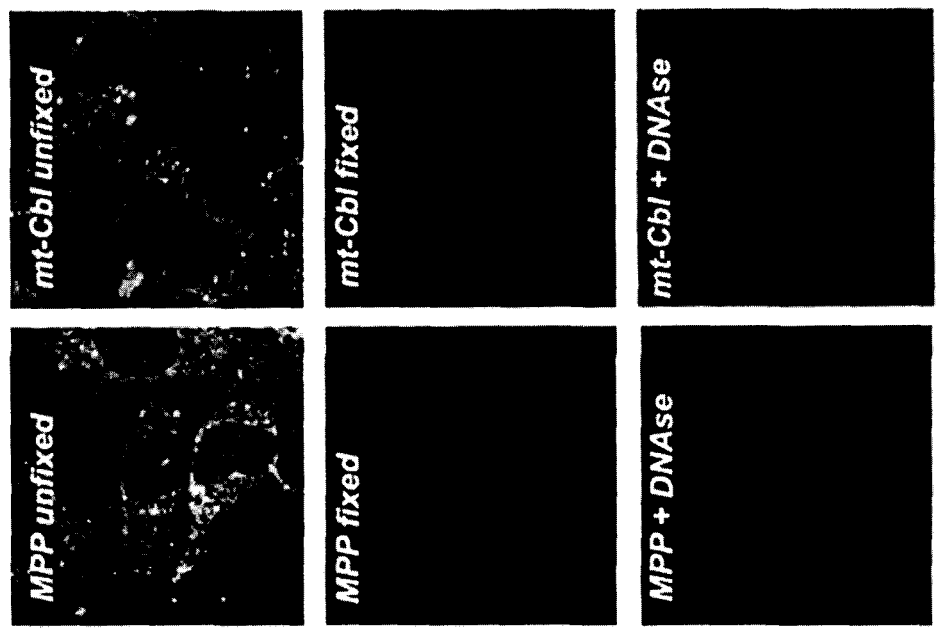
FIG. 8 shows DNA alkylation by mt-Cbl. (A) Cbl retains the MPP in mitochondria after cellular fixation. Fluorescently labeled mt-Cbl and the control peptide (MPP) were incubated with live HeLa cells and mitochondrial localization was observed in unfixed cells. Under fixation and permeabilization conditions, mt-Cbl maintained mitochondrial localization while the MPP diffused to the nucleus and cytoplasm. Following this, cells were incubated with DNase (10 units) to catalyze the cleavage of DNA. Treatment with DNase results in diffusion of mt-Cbl localization. (B) Alkylation activity of mtCbl. Alkylation activity was monitored by measuring the absorbance of 4-(4-Nitrobenzyl)pyridine upon alkylation with Cbl. Attachment of the mitochondria-targeting peptide reduced the alkylating ability of the conjugated chlorambucil approximately two fold compared to Cbl alone. (C) Crosslinking of isolated DNA by mtCbl and Cbl. DNA treated with varying concentrations of mtCbl or Cbl (2-200 μM) resulted in concentration-dependent crosslink formation (left). Time-dependent DNA crosslinking (varied from 5-60 min) by mtCbl and Cbl (right).
Figure 8C:
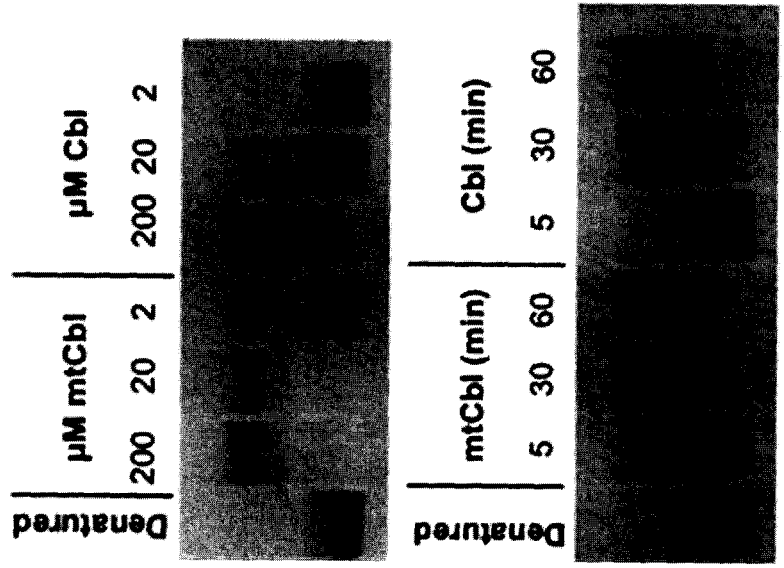
Figure 8B:
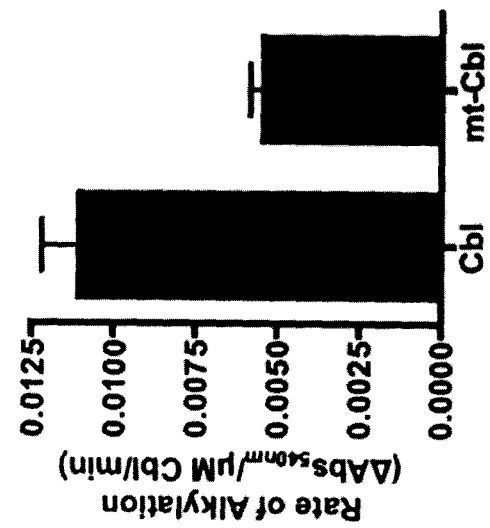

The alkylating activity of MPP-Cbl within mitochondria was also assessed by incubating HeLa cells with the conjugate, allowing alkylation to occur, and then fixing the cells and permeabilizing their membranes (FIG. 8A). The MPP-Cbl conjugate maintained its mitochondrial localization, even upon membrane permeabilization, while the MPP control peptide diffused from the mitochondria to the cytoplasm and nucleus upon membrane disruption. Following fixation and permeabilization, cells were treated with DNase to fragment the DNA and this resulted in diffusion of MPP-Cbl (FIG. 8A). These observations suggest that MPP-Cbl reacts within mitochondria.

Figure 1E:
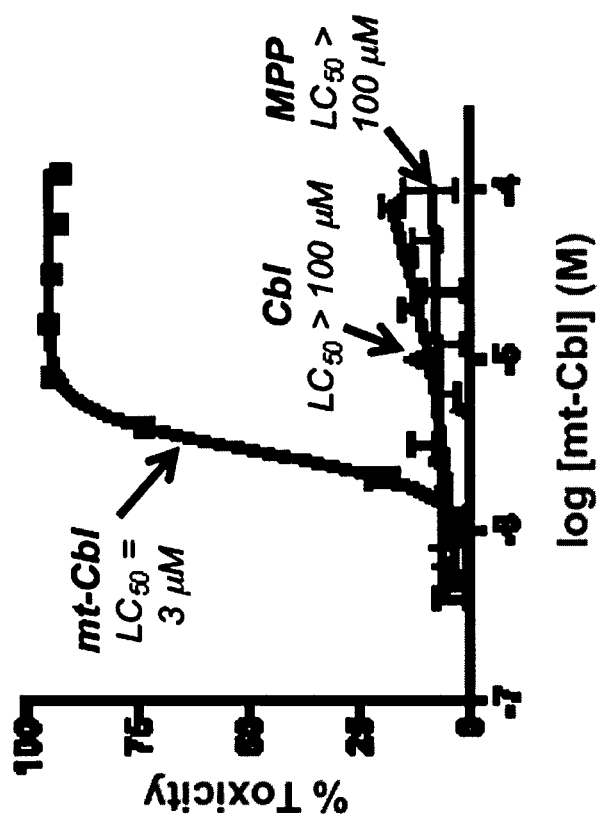
Figure 1G:
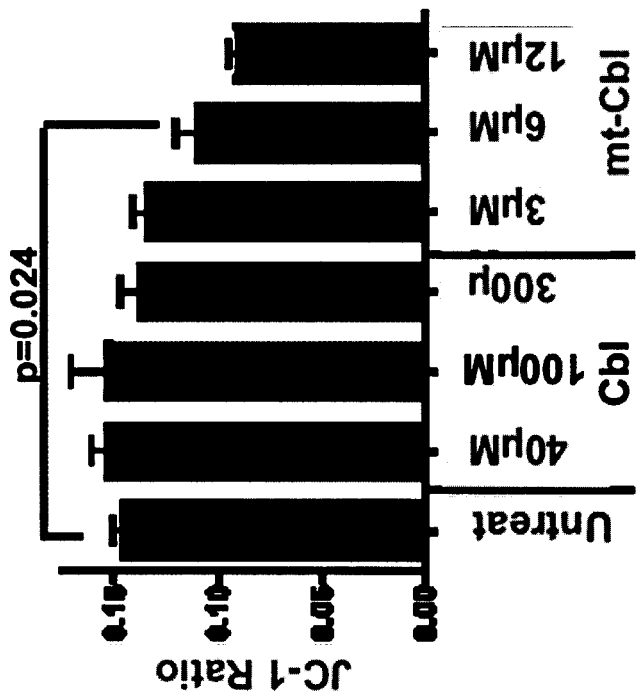
Figure 1F:
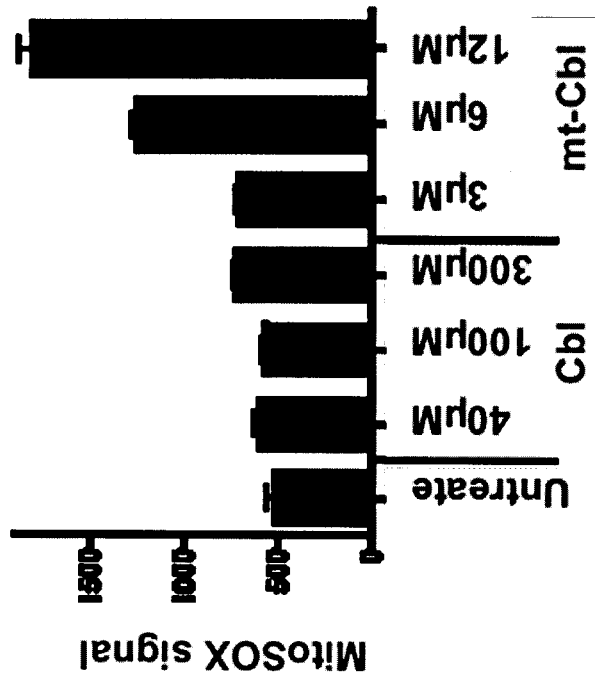

The cytotoxicity of MPP-Cbl towards HeLa cells was compared to the parent peptide and unconjugated Cbl. Using a cell viability assay, a 100-fold increase in potency was observed with MPP-Cbl compared to Cbl (FIG. 1E). The parent peptide did not show appreciable toxicity in the concentration range tested, confirming that the cell death resulted from the activity of the drug and not the vector. To verify that this increase in potency was due to perturbation of mitochondrial function, organellar membrane potential and superoxide levels were assessed. Mitochondrial DNA lesions have been shown to increase mitochondrial superoxide levels and depolarize this organelle's membrane[8]. Both these observations were noted upon MPP-Cbl treatment but not with Cbl (FIGS. 1F and 1G), an agent whose activity is linked to alkylation of the nuclear genome. These data support our hypothesis that MPP-Cbl is specifically acting upon a mitochondrial target. To evaluate the activity and specificity of mt-Cbl in leukemia cells, we assessed its toxicity in a panel of leukemia cell lines. Similar levels of toxicity were observed. For example, in HL60 cells, mt-Cbl again exhibited an increase in potency compared to Cbl (Table 4), with an EC50 of 34 and 6.8 µM for Cbl and mt-Cbl, respectively.

Figure 2:
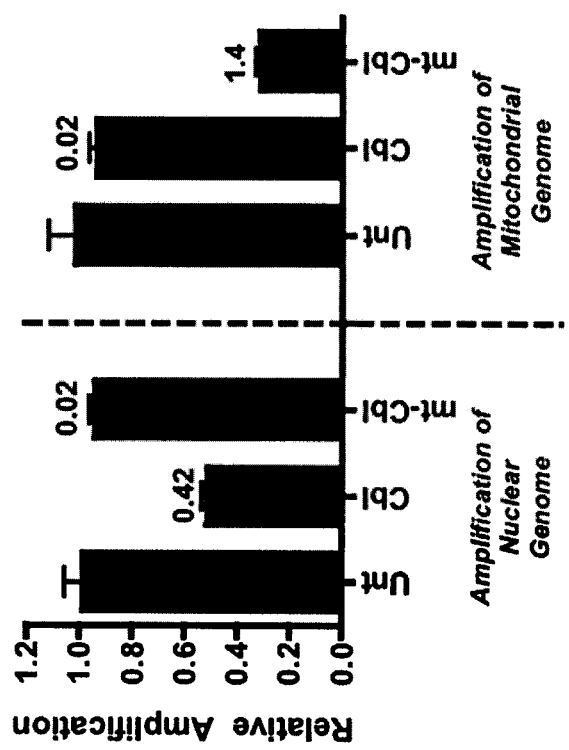
FIG. 2 shows Cbl and mt-Cbl induce DNA damage in different organelles. Relative amplification of 17.7 kb nuclear and 8.9 kb mitochondrial DNA segments. HL60 cells were treated with Cbl (150 µM) or mt-Cbl (3 µM) for 2 hr prior to PCR analysis. Lesions/10 kb values are included above the graph bars.

The alkylation of nuclear versus mitochondrial DNA was quantitatively assessed by comparing the efficiency of PCR amplification of the two genomes. HL60 cells were treated with either Cbl or mt-Cbl, and damage of the nuclear and mitochondrial genomes was assessed independently. A 17.7 kb segment of nuclear DNA at the β-globin gene and an 8.8 kb fragment of mitochondrial DNA were analyzed. Cbl primarily damaged nuclear DNA with very few mitochondrial lesions, whereas mt-Cbl caused a significant reduction of mitochondrial DNA amplification with minimal effect on the nuclear genome (FIG. 2).

Previous studies exploiting cell-penetrating peptides for mixed cytoplasmic and nuclear intracellular delivery of Cbl documented only a ~10-fold increase in activity[9], suggesting that the mitochondrial delivery of Cbl leads to a further augmentation in activity. This augmentation surpasses what would be expected if enhanced uptake was the underlying factor, as the MPP used here has comparable, but not increased uptake relative to cell penetrating peptides used previously.[4] The increased activity likely results instead from key differences between the mitochondrial genome and its nuclear counterpart. The lack of introns in the mitochondrial genome increases the probability that damage will target an essential DNA sequence[10]. Moreover, the mitochondrial genome is not as packaged as the nuclear genome making it 500 times more sensitive to DNA damaging agents[11]. In addition, mitochondrial pathways of DNA repair are not as comprehensive as those operative in the nucleus[12]. All of these factors may contribute to the 100-fold increase in potency observed.

Figure 3A:
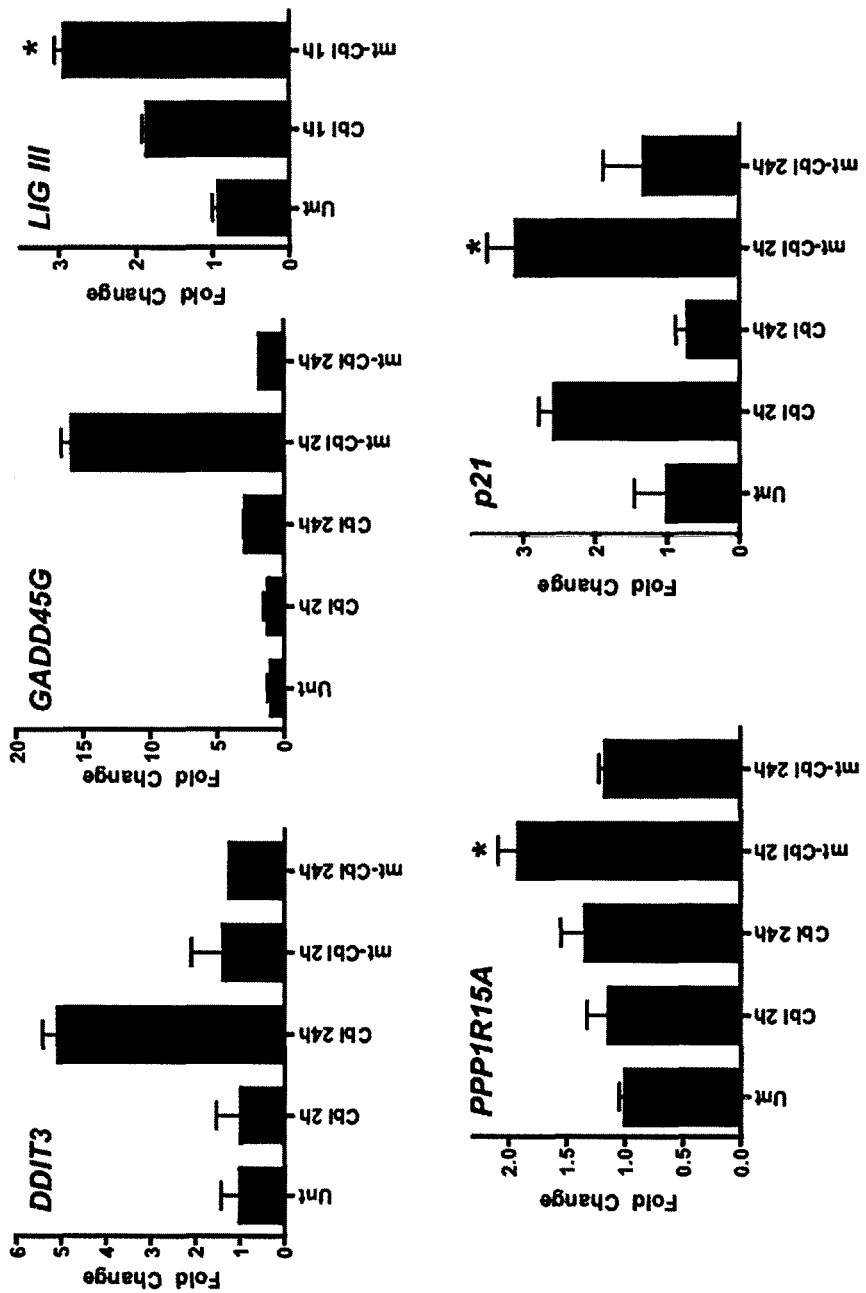
FIG. 3 shows differing gene expression profiles in response to DNA damage by Cbl and mt-Cbl. (A) A qPCR array for genes involved in detecting DNA damage and inducing apoptosis was used to assess RNA expression profiles of HL60 cells treated with LC25 doses of Cbl or mt-Cbl for 2 or 24 hr. To assess Ligase III expression, cells were treated with LC50 doses of Cbl or mt-Cbl for 1 hr. *MPP change in expression subtracted from mt-Cbl result. Mean values plotted, n=3, error bars equal SEM. (B) Results from qPCR array highlighting hits with greater than ≥4-fold change in expression. (C) Protein expression levels of qPCR hits. HL60 cells were treated with LC25 doses of Cbl (17 µM) or mt-Cbl (3 µM) prior to assessment of protein levels by immunoblotting. All blots were performed after a 2 hour treatment except for the DDIT3 levels, which were assessed after a 24 hour Cbl incubation. β-actin was used as a loading control. (D) Expression levels of GADD45G pathway effector proteins involved in mt-Cbl toxicity. HL60 cells were treated with Cbl, MPP or mt-Cbl and protein levels were assessed using immunoblotting. β-actin was used as a loading control. Proteins downstream of the GADD45G pathway, JNK and p38, are shown to be upregulated upon Cbl and mt-Cbl treatment. Furthermore, Cbl appears to activate p38 while mt-Cbl activates JNK.
Figure 3B:
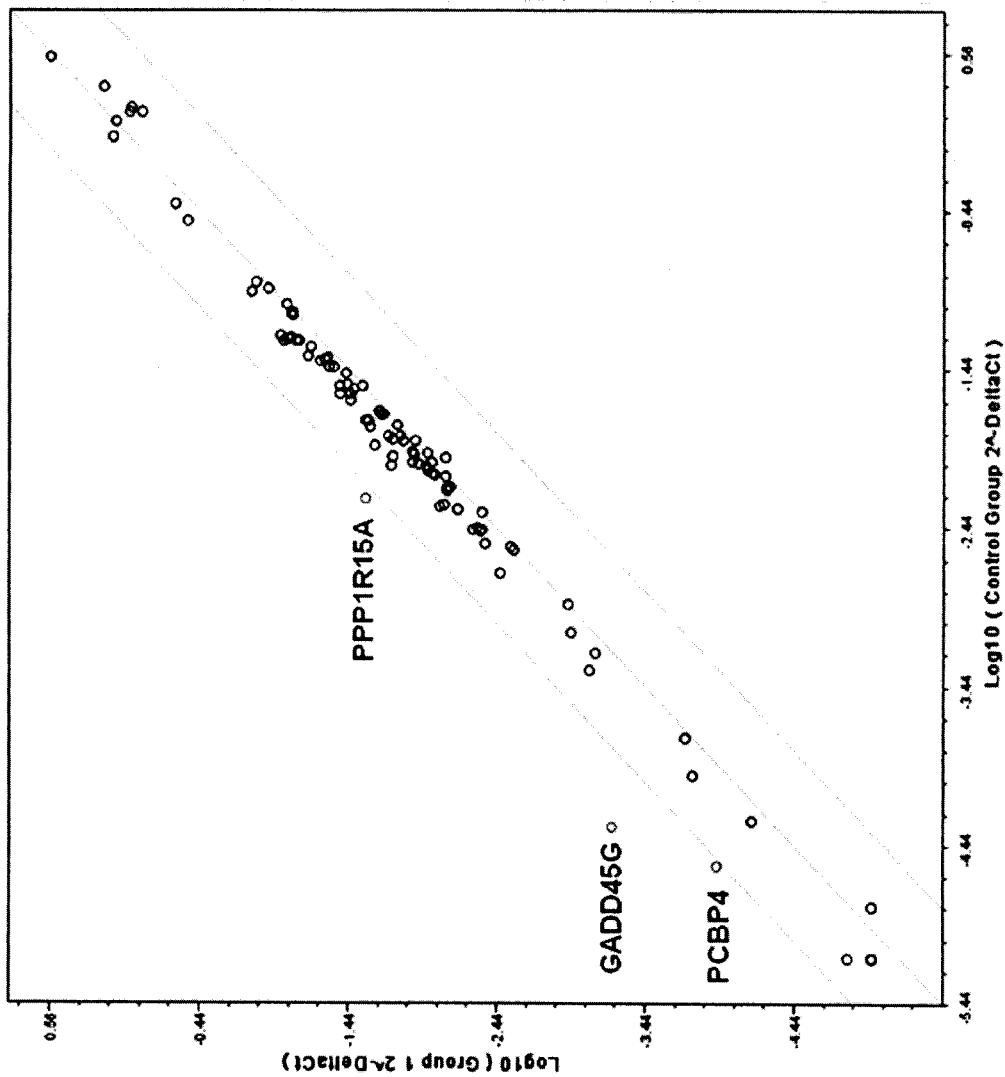

A quantitative real-time PCR array was used to assess a panel of 84 genes, ten of which have mitochondrial activity (Table 3). These ten genes are known to be involved in DNA damage sensing, repair, apoptosis, and cell cycle arrest. Genes were considered to be differentially expressed if they showed a ≥4-fold change compared to untreated cells (FIG. 3B), and hits were confirmed with three biological replicates using individually synthesized PCR primers. This analysis revealed that different pathways are activated when nuclear versus mitochondrial DNA alkylation occurs. DDIT3/GADD153 exhibited a 5-fold increase in expression in response to Cbl but no change with mt-Cbl, suggesting that this gene is primarily involved in responding to nuclear DNA damage. Two other genes were upregulated to a greater extent with mt-Cbl relative to Cbl alone: PPP1R15A/GADD34 (4-fold) and GADD45G (15-fold) (FIGS. 3A and 3B). p21 was overexpressed in the presence of both mt-Cbl and Cbl. These changes in mRNA levels were confirmed to lead to a corresponding change in protein expression (FIG. 3C). Interestingly, none of the genes mentioned above that are known to be mitochondrially targeted were affected.

The Growth Arrest and DNA Damage-inducible (GADD) family of genes are known to be involved in apoptosis and cell-cycle arrest[32], and the p21 protein is also known to play an important role in DNA damage sensing. p21 has been shown to interact with GADD45G[33], which can activate p38 or JNK pathways[34]. The activation of these pathways was assessed with immunoblotting following treatment with Cbl or mt-Cbl, and interestingly, differ-ential activation was observed, with Cbl activating p38 and mt-Cbl activating JNK (FIG. 3D). These results show that different cellular responses are mounted when the same compound is targeted to distinct intracellular sites.

The levels of Ligase III were also investigated in Cbl and mt-Cbl treated cells. This ligase, present in both the nucleus and mt, is the only ligase in the latter organelle and is involved in the repair of most forms of DNA damage[35]. Therefore, in response to mt-Cbl induced damage of the mitochondrial genome, an increase in expression of this gene should be observed. Indeed, this was detected in cells treated with mt-Cbl (FIG. 3A; FIG. 3C).

TABLE 3

List of mitochondrially-targeted proteins included in qPCR array.

| Gene Symbol | Gene Name | Cellular Function |
| --- | --- | --- |
| OGG1 | 8-oxoguanine DNA glycosylase | Damaged DNA binding, Base-excision repair |
| RAD18 | RAD18 homolog (S. cerevisiae) | Damaged DNA binding |
| APEX1 | APEX nuclease | Base-excision repair |
| MUTYH | mutY homolog (E. coli) | Base-excision repair, mismatch repair |
| NTHL1 | nth endonuclease III-like 1 (E. coli) | Base-excision repair |
| UNG | uracil-DNA glycosylase | Base-excision repair |
| MRE11A | meiotic recombination 11 homolog A (S. cerevisiae) | Double-strand break repair |
| RAD50 | RAD50 homolog (S. cerevisiae) | Double-strand break repair |
| MLH1 | mutL homolog 1 (E. coli) | Mismatch repair |
| AIFM1 | apoptosis-inducing factor, mitochondrion-associated 1 | Apoptosis |

Figure 4:
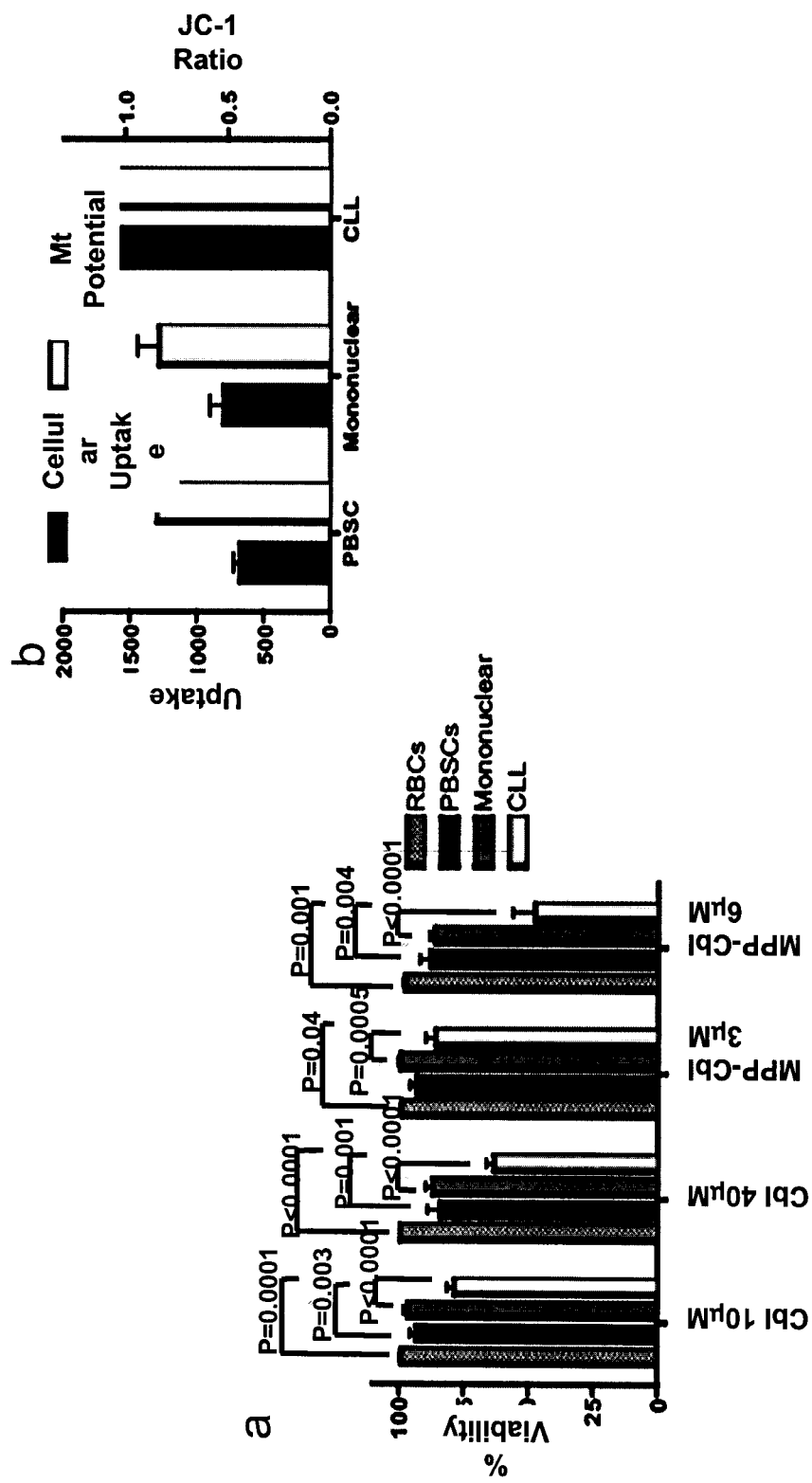
FIG. 4 shows the evaluation of MPP-Cbl activity and therapeutic window in primary CLL cells. (A) Cbl and MPP-Cbl activity evaluated at LC25 and LC50 in red blood cells (RBCs) (healthy donors), peripheral blood stem cells (PBSCs) (healthy donors), mononuclear cells (healthy donors) and CLL patient cells. Both Cbl and MPP-Cbl were more selectively toxic to CLL patient samples cells compared to those derived from healthy donors. Percent viability was determined by FACS analysis of Annexin V/Sytox Red cell staining. Hemolytic activity of RBCs with Cbl and MPP-Cbl was found to be minimal at the concentrations used in this experiment. Mean values plotted, n>5, error bars are s.e.m. Two-tailed t-test used to determine P values. (B) MPP uptake and mitochondrial membrane potential for peripheral blood cells, mononuclear cells and CLL patient cells. Uptake of thiazole orange (to)-MPP measured by flow cytometry showed higher levels of peptide uptake in CLL cells. Mitochondrial membrane potential as measured by FACS analysis of JC-1 staining—with a decreasing JC-1 ratio indicative of lower mitochondrial membrane potential—indicated a higher mitochondrial membrane potential for CLL patient cells in comparison to PBSCs and mononuclear cells from healthy donors. Mean values plotted, n=3, error bars are s.e.m.

Cbl is a clinically used therapeutic indicated for the treatment of leukemia.[6] To determine whether the MPP-Cbl conjugate would show enhanced activity over the parent compound in primary cancer cells, we assessed toxicity profiles for B cells isolated from chronic lymphocytic leukemia (CLL) patients. To assess normal cells and evaluate whether the compound exhibited a therapeutic window, peripheral blood stem cells (PBSCs) and mononuclear cells from healthy donors were used to evaluate the therapeutic window of MPP-Cbl. With MPP-Cbl treatment, we observed activity against CLL patient cells that was significantly lower in healthy cells, indicating that a therapeutic window exists for the peptide conjugate (FIG. 4A). Furthermore, MPP-Cbl showed nominal hemolysis levels at the concentrations used in this study (FIG. 4A) suggesting a lack of toxicity to red blood cells at concentrations where leukemic cells were ablated.

To investigate the source of the therapeutic window, we evaluated the cellular uptake of the MPP in the CLL cells, mononuclear cells, and PBSCs. MPP uptake in CLL cells was higher than in healthy cells, indicating that higher drug concentrations would be achieved in these cells (FIG. 4B). Moreover, a higher relative mitochondrial membrane potential was observed with CLL cells (FIG. 4B), indicating that there would be a greater driving force for mitochondrial accumulation in this cell type. This difference in mitochondrial membrane potential between cancer and healthy cells has been widely reported[13] and differential drug toxicity due to this characteristic has also been previously observed, such as in studies with Rhodamine 123 and MKT-077[14-16]. However, here a drug is being delivered that is not a delocalized lipophilic cation; and thus, the peptide carrier is providing the specificity. Therefore, MPPs present a general vector for mitochondrial drug delivery that preserves therapeutic window.

Figure 5:
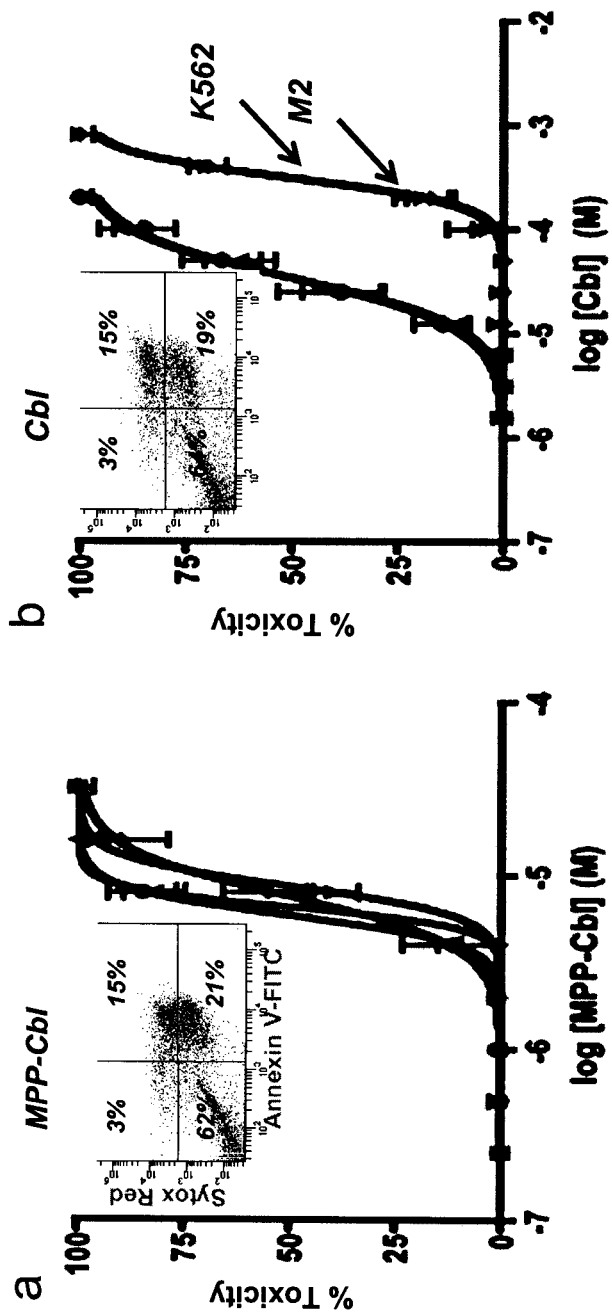
FIG. 5 shows the toxicity of MPP-Cbl in cell lines exhibiting drug resistance and apoptotic resistance. (A) Toxicity of MPP-Cbl towards a panel of leukemia cell lines (M2, K562, HL60 and U937). Mean values plotted, n>3, error bars are s.e.m. Inset: FACS analysis of HL60 Annexin V-FITC (A-FITC)/Sytox Red (SR) cell staining after treatment with 6 μM MPP-Cbl. Indicated are the percent of population in each quadrant (A-FITC−/SR−: Alive, FITC+/SR−: Apoptotic, A-FITC−/SR+: Necrotic, A-FITC+/SR+: Dead). (B) Toxicity of Cbl with leukemia cell lines showed two distinct populations with HL60 and U937 being sensitive to Cbl and K562 and M2 being resistant to Cbl. Inset same as part (a) but with 34 μM Cbl. (C) Apoptotic resistance in Cbl-resistant cell lines. Response of leukemia cell lines to staurosporine as measured by FACS analysis of Annexin V/Sytox Red stained cells (black bars). Graphed are percent viable cells. Staurosporine treatment induced less cell death in the K562 and M2 cell lines compared to HL60 and U937. K562 and M2 cell lines show higher levels of Bcl-XL expression (white bars) (See FIG. 6 for Western Blot). (D) Toxicity of MPP-Cbl in WT or Cbl-resistant cells (CblR). Cells were as in (A). Cbl alone did not show an increase in the apoptotic cell population in CblR, however, an apoptotic response with MPP-Cbl treatment was observed for both WT and CblR cell lines.
Figure 5:
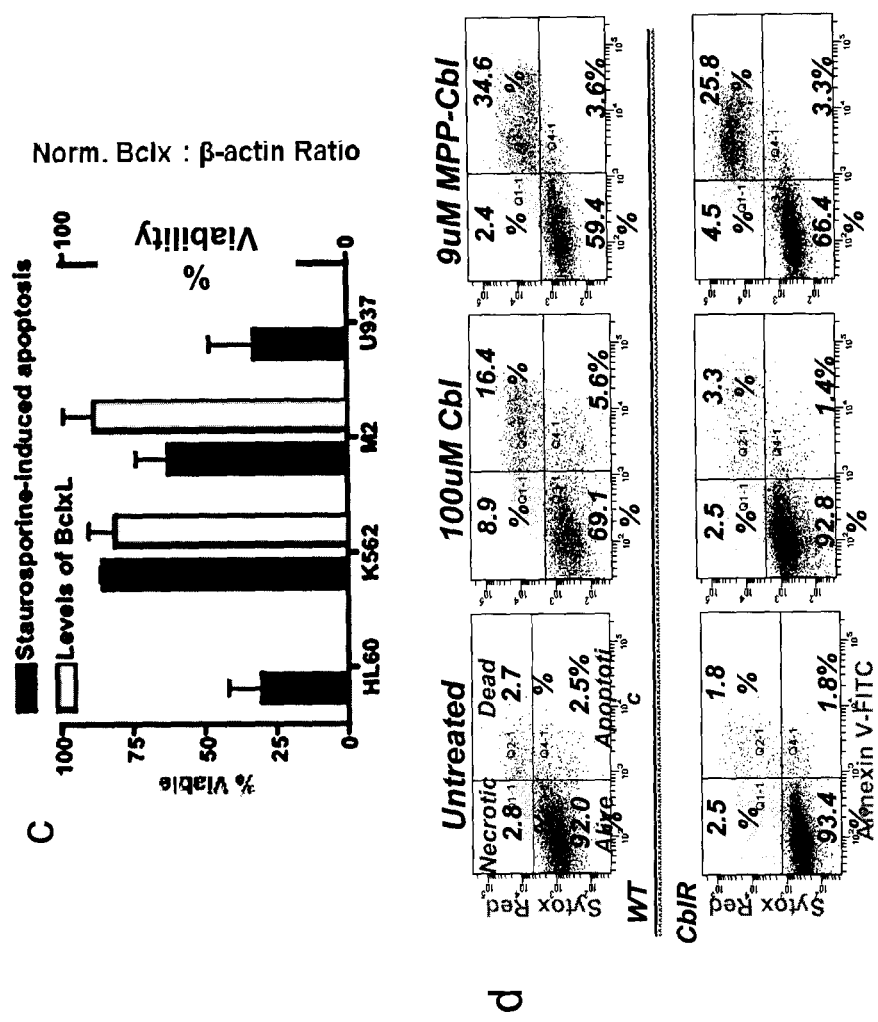

Given that Cbl resistance has been detected in leukemia[17, 18], we investigated if delivery of Cbl to mitochondria would alter the effectiveness of drug resistance mechanisms. We tested the activity of the unmodified drug in a panel of myeloid and lymphoid cell lines and observed that in two cell lines (K562 and OCI-M2), the parent drug had attenuated potency. These two cell lines were approximately 10-fold more resistant to Cbl than the rest of the cohort (FIG. 5B and Table 4).

TABLE 4

Summary of $LC_{50}$ values in leukemia cell line panel.

| Cell Line | Cbl $LC_{50}$ | MPP-Cbl $LC_{50}$ |
| --- | --- | --- |
| M2 | 311 ± 24 μM | 7.5 ± 1 μM |
| K562 | 306 ± 26 μM | 8.7 ± 0.4 μM |
| LY17 | 55 ± 7 μM | 8.3 ± 1 μM |
| HL60 | 34 ± 6 μM | 6.8 ± 0.6 μM |
| U937 | 34 ± 5 μM | 5.9 ± 0.7 μM |
| AML2 | 28 ± 3 μM | 6.4 ± 0.4 μM |
| DAUDI | 27 ± 7 μM | 9.8 ± 0.8 μM |

Figure 6:
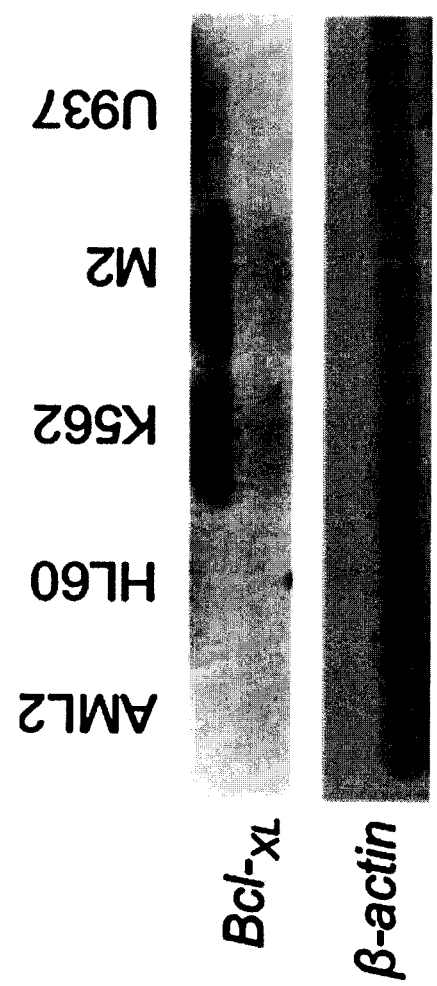
FIG. 6 shows a Western blot of $Bcl_{XL}$ and β-actin levels in leukemia cell lines. Western blot analysis was performed as described above. Total protein levels were determined via BCA assay and equal protein was loaded in each well as seen with β-actin loading control.

Many cancer cell types are known to increase thresholds for apoptotic induction by altering levels of pro-apoptotic or anti-apoptotic factors, leading to chemotherapeutic resistance. To determine whether the Cbl-resistant cells were generally resistant to apoptosis, we tested the sensitivity of these lines to staurosporine, an apoptosis-inducing agent. Interestingly, the two Cbl-resistant cell lines showed reduced rates of apoptotic induction (FIG. 5C). Since over-expression of anti-apoptotic factors is one mechanism of apoptotic resistance[19, 20], we investigated the expression level of the anti-apoptotic protein $Bcl_{XL}$. $Bcl_{XL}$ has been shown previously to be over-expressed in certain cancers and its anti-apoptotic activity is thought to contribute to drug resistance[21]. Indeed, in these two Cbl-resistant lines, we observed a much higher level of $Bcl_{XL}$ than in the sensitive lines (FIG. 5C, FIG. 6). This suggests that $Bcl_{XL}$ overexpression, and the resulting suppression of apoptosis, may underlie the resistance to Cbl. When the activity of MPP-Cbl was tested in this panel, potentiation was observed in all lines tested (FIG. 5A). In addition, the mechanism of cell death for Cbl and the MPP conjugate appeared similar, with early apoptotic cells apparent by flow cytometry (Inset, FIGS. 5A and 5B). The fact that the MPP-Cbl conjugate still exhibits high levels of cytotoxicity in these apoptosis-resistant cell lines indicates that the delivery of a toxic drug to mitochondria presents an effective means to overcome this mechanism commonly employed by cancer cells to resist the action of drugs.

Figure 7:
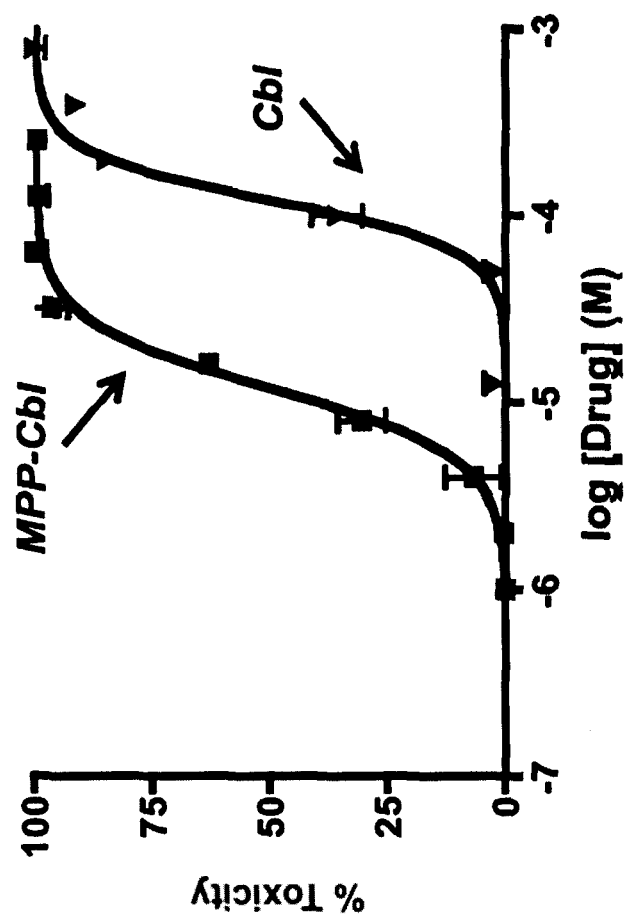
FIG. 7 shows a comparison of LC50 in A2780 wildtype cells between Cbl and MPP-Cbl. A2780 wildtype cells were treated with Cbl (right curve) and MPP-Cbl (left curve) as described above. Toxicity was analyzed with the CCK8 assay.

Another major form of drug resistance in cancer cells results from the overexpression of enzymes or other factors that facilitate chemical deactivation of pharmacophores. For Cbl, inactivation via glutathione modification is a common mechanism of resistance. Addition of the glutathione tripeptide to Cbl, a reaction catalyzed by glutathione-S-transferase (GST), not only results in the inactivation of Cbl[22], it also promotes efflux from the cell by pumps that recognize glutathione-modified xenobiotics[23]. In order to analyze whether MPP-Cbl would be able to evade drug resistance arising from this type of chemical inactivation, we tested activity of this conjugate in a Cbl-resistant ovarian cancer cell line known to overexpress the cytoplasmic GST-μ isoform[24]. Using the Annexin-V apoptosis assay, we observed that Cbl was able to induce cell death in the wild-type cell line but in the Cbl-resistant line, toxicity was insignificant, even at 100 μM (FIG. 5D). Interestingly, MPP-Cbl was able to induce cell death at a much lower concentration (9 μM), and this value was comparable in both the wild-type and resistant line. This finding was also confirmed through a cell viability assay (FIG. 7). Conjugation of the MPP to Cbl appears to limit modification and inactivation by the cytoplasmic GST-μ. The comparable activity between the wildtype and Cbl-resistant lines supports the notion that targeting and sequestering drugs to the mitochondria also allows evasion of chemical mechanisms of drug resistance.

We have demonstrated the advantages of targeting the mitochondria of cancer cells for combating drug resistance and show that mitochondrial delivery of Cbl results in a significant gain of potency. Importantly, even though the MPP directs Cbl to a novel target—the mitochondrial genome, a therapeutic window was maintained due to differential membrane potentials between CLL cells and healthy cells. These studies also illustrate that mitochondrial compartmentalization of Cbl allows for evasion of drug resistance both through biochemical mechanisms—perturbations in the apoptotic pathway, and chemical mechanisms—drug inactivation. As many drug resistance mechanisms involve factors localized within the plasma membrane as well as the cytoplasm (e.g. efflux pumps and inactivating enzymes), drug sequestration into the mitochondria serves as a means to evade multiple resistance mechanisms. Mitochondrial delivery as a means of "repurposing" FDA-approved drugs currently used in the clinic appears to therefore be a worthwhile strategy to pursue in the development of new anticancer agents.

Although preferred embodiments of the invention have been described herein, it will be understood by those skilled in the art that variations may be made thereto without departing from the spirit of the invention or the scope of the appended claims. All references disclosed herein are incorporated in the entirety by reference.

REFERENCES

1. Muratovska, A., Lightowlers, R. N., Taylor, R. W., Wilce, J. A. & Murphy, M. P. *Adv Drug Deliv Rev* 49, 189-98 (2001).
2. Taylor, R. C., Cullen, S. P. & Martin, S. J. *Nat Rev Mol Cell Biol* 9, 231-41 (2008).
3. Hanahan, D. & Weinberg, R. A. *Cell* 100, 57-70 (2000).
4. Horton, K. L., Stewart, K. M., Fonseca, S. B., Guo, Q. & Kelley, S. O. *Chem Biol* 15, 375-82 (2008).
5. Yousif, L. F., Stewart, K. M., Horton, K. L. & Kelley, S. O. *Chembiochem* 10, 2081-8 (2009).
6. Begleiter, A., Mowat, M., Israels, L. G. & Johnston, J. B. *Leuk Lymphoma* 23, 187-201 (1996).
7. Carreon, J. R., Stewart, K. M., Mahon, K. P., Jr., Shin, S. & Kelley, S. O. *Bioorg Med Chem Lett* 17, 5182-5 (2007).
8. Santos, J. H., Hunakova, L., Chen, Y., Bortner, C. & Van Houten, B. *J Biol Chem* 278, 1728-34 (2003).
9. Myrberg, H., Zhang, L., Mae, M. & Langel, U. *Bioconjug Chem* 19, 70-5 (2008).
10. Preston, T. J., Abadi, A., Wilson, L. & Singh, G. *Adv Drug Deliv Rev* 49, 45-61 (2001).
11. Allen, J. A. & Coombs, M. M. *Nature* 287, 244-5 (1980).
12. Singh, G. & Maniccia-Bozzo, E. *Cancer Chemother Pharmacol* 26, 97-100 (1990).
13. Davis, S., Weiss, M. J., Wong, J. R., Lampidis, T. J. & Chen, L. B. *J Biol Chem* 260, 13844-50 (1985).
14. Modica-Napolitano, J. S. & Aprille, J. R. *Adv Drug Deliv Rev* 49, 63-70 (2001).
15. Modica-Napolitano, J. S. & Aprille, J. R. *Cancer Res* 47, 4361-5 (1987).
16. Modica-Napolitano, J. S. et al. *Cancer Res* 56, 544-50 (1996).
17. Petrini, M. et al. *Br J Haematol* 85, 409-10 (1993).
18. Pepper, C., Thomas, A., Hoy, T. & Bentley, P. *Br J Haematol* 104, 581-8 (1999).
19. Reed, J. C. *Oncogene* 17, 3225-36 (1998).
20. Lowe, S. W. & Lin, A. W. *Carcinogenesis* 21, 485-95 (2000).
21. Minn, A. J., Rudin, C. M., Boise, L. H. & Thompson, C. B. *Blood* 86, 1903-10 (1995).
22. Yang, W. Z., Begleiter, A., Johnston, J. B., Israels, L. G. & Mowat, M. R. *Mol Pharmacol* 41, 625-30 (1992).
23. Barnouin, K. et al. *Br J Cancer* 77, 201-9 (1998).
24. Horton, J. K. et al. *Biochem Pharmacol* 58, 693-702 (1999).
25. Horton, K. L.; Kelley, S. O. *J. Med. Chem.* 52, 3293-3299 (2009).
26. Horton, K. L.; Stewart, K. M.; Fonseca, S. B.; Guo, Q.; Kelley, S. O. *Chem. Biol.* 15, 375-382 (2008)
27. Carreon, J. R.; Stewart, K. M.; Mahon, K. P., Jr.; Shin, S.; Kelley, S. O. *Bioorg. Med. Chem. Lett.* 17, 5182-5185 (2007).
28. Cullis, P. M.; Green, R. E.; Malone, M. E. *J. Chem. Soc. Perkin Trans.* 2, 1503-1511 (1995).
29. Frezza, C.; Cipolat, S.; and Scorrano, L. *Nat. Protoc.* 2, 287-295 (2007).
30. Sunters, A.; Springer, C. J.; Bagshawe, K. D.; Souhami, R. L.; and Hartley, J. A. *Biochem. Pharmacol.* 59-64 (1992).
31. Santos, J. H., Meyer, J. N., Mandavilli, B. S., and Van Houten, B. *Methods Mol. Biol.,* 183-199 (2006).
32. Smith, M. L., and Fornace, A. J., Jr. *Mutat. Res.* 340, 109-124 (1996).
33. Fan, W., Richter, G., Cereseto, A., Beadling, C., and Smith, K. A. *Oncogene* 18, 6573-6582 (1999).
34. Lu, B., Yu, H., Chow, C., Li, B., Zheng, W., Davis, R. J., and Flavell, R. A. *Immunity* 14, 583-590 (2001).
35. Lakshmipathy, U., and Campbell, C. *Mol. Cell. Biol.* 19, 3869-3876 (1999).

The invention claimed is:

1. A compound comprising a mitochondrial penetrating peptide (MPP) conjugated to an anticancer compound, wherein the MPP is SEQ ID NO: 7, and the anticancer compound is a DNA intercalator, an alkylating agent, a transcription inhibitor, a DNA enzyme inhibitor, or a DNA synthesis inhibitor.

2. The compound of claim 1, wherein the anticancer compound is a DNA intercalator that is an isoquinoline alkaloid, acridine, anthracycline or furocoumarin.

3. The compound of claim 1, wherein the anticancer compound is a DNA intercalator that is berberine, proflavine, daunorubicin, doxorubicin, thalidomide, psoralen or ethidium bromide.

4. The compound of claim 1, wherein the anticancer compound is an alkylating agent that is a nitrogen mustard, nitrosourea, sulphur mustard or platinum compound.

5. The compound of claim 1, wherein the anticancer compound is an alkylating agent that is melphalan, bendamustine, carmustine, bis(2-chloroethyl sulfide), sulfur sesquimustard, cisplatin, satraplatin, sitomycin, dacarbazine, chlorambucil, mitozolomide or temozolomide.

6. The compound of claim 1, wherein the anticancer compound is a transcription inhibitor that is a polypeptide antibiotic.

7. The compound of claim 6, wherein the polypeptide antibiotic is actinomycin D.

8. The compound of claim 1, wherein the anticancer compound is a DNA enzyme inhibitor that is a topoisomerase inhibitor.

9. The compound of claim 8, wherein the topoisomerase inhibitor is etoposide, mitoxantrone, amsacrine, teniposide or irinotecan.

10. The compound of claim 1, wherein the anticancer compound is a DNA synthesis inhibitor that is a DNA analog.

11. The compound of claim 10, wherein the DNA analog is fludarabine, mercaptopurine, thioguanine, pentostatin, cladribine or floxuridine.

12. The compound of claim 1, wherein the anticancer compound is an enzyme inhibitor that is a glutathione s-transferase inhibitor or ATP synthase inhibitor.

13. The compound of claim 12, wherein the glutathione s-transferase inhibitor is etacrynic acid.

14. The compound of claim 12, wherein ATP synthase inhibitor is oligomycin.

15. The compound of claim 1, wherein the anticancer compound is conjugated to the C-terminus of the MPP.

16. The compound of claim 1 being SEQ ID NO: 7 conjugated to chlorambucil.

17. A pharmaceutical composition comprising the compound of claim 1 and a pharmaceutically acceptable carrier.

18. A library of compounds comprising a plurality of compounds of claim 1.

19. A method of treating cancer comprising administering to a subject a therapeutically effective amount of the composition compound of claim 16, wherein the cancer is selected from the group consisting of leukemia, lymphoma, and ovarian cancer.

20. A method of inducing apoptosis in a cancer cell comprising administering a therapeutically effective amount of the composition compound of claim 16, wherein the cancer cell is from a cancer selected from the group consisting of leukemia, lymphoma, and ovarian cancer.

\* \* \* \* \*